(12) United States Patent
Schweighoffer et al.

(10) Patent No.: US 6,251,590 B1
(45) Date of Patent: Jun. 26, 2001

(54) DIFFERENTIAL QUALITATIVE SCREENING

(75) Inventors: Fabien Schweighoffer, Vincennes; Laurent Bracco, Paris; Bruno Tocque, Courbevoie, all of (FR)

(73) Assignee: ExonHit Therapeutics S.A., Paris (FR)

( * ) Notice: Subject to any disclaimer, the term of this patent is extended or adjusted under 35 U.S.C. 154(b) by 0 days.

(21) Appl. No.: 09/046,920

(22) Filed: Mar. 24, 1998

(30) Foreign Application Priority Data

Mar. 11, 1998 (FR) .................................................. 98 02997

(51) Int. Cl.⁷ .............................. C12Q 1/68; C12P 19/34; C07H 21/02; C07H 21/04

(52) U.S. Cl. ........................... 435/6; 435/91.1; 435/91.2; 435/91.21; 435/91.4; 435/91.51; 536/23.1; 536/23.2; 536/23.5; 536/24.3; 536/24.31; 536/24.33

(58) Field of Search .............................. 435/6, 91.1, 91.2, 435/91.21, 91.4, 91.51; 536/23.1, 23.2, 23.5, 24.3, 24.31, 24.32, 24.33

(56) References Cited

U.S. PATENT DOCUMENTS

| 5,445,934 | 8/1995 | Fodor et al. .............................. 435/6 |
| 5,521,297 | * 5/1996 | Daggett et al. . |
| 5,643,729 | * 7/1997 | Taniguchi et al. . |
| 5,679,541 | 10/1997 | Bonine et al. ....................... 435/69.1 |

FOREIGN PATENT DOCUMENTS

| 0 806 478 | 11/1997 | (EP) . |
| 2 664 287 | 1/1992 | (FR) . |
| WO 94 12631 | 6/1994 | (WO) . |
| WO 95 27052 | 10/1995 | (WO) . |
| WO 96 26272 | 8/1996 | (WO) . |
| WO 96 30512 | 10/1996 | (WO) . |
| WO 97 04092 | 2/1997 | (WO) . |
| WO 97/27317 | 7/1997 | (WO) . |
| WO 97/29212 | 8/1997 | (WO) . |
| WO 97 46679 | 12/1997 | (WO) . |
| WO 98 02576 | 1/1998 | (WO) . |

OTHER PUBLICATIONS

Zhao et al Gene vol. 156 pp. 207–213 1995.*
Cooper, et al., "Gene Therapy Advances: Utilization of Alternative Splicing as a Control Element in the Chimeric Enzyme/Prodrug Therapy (CEPT) Approach to Primary and Metastatic Tumors" *Journal of Clinical Ligand Assay.* 19:80–84 (1996).
Alphey, L., "PCR–Based Method Isolation of Full–length Clones and Splice Variants from cDNA Libraries" *Biotechniques* 22:481 (1997).
Bonass, et al., "The Rat Amelogenin Gene—Some Aspects of Evolution and Expression" *Advances in Dental Research* 10:182–186 (1996).

Miller, R. D. and Riblet, R., "Improved Phenol Emulsion DNA Reassociation Technique (PERT) using Thermal Cycling" *Nucletic Acids Research* 23:2339–2340 (1995).
Ardley, et al., "Rapid Isolation of Genomic Clones for Individual Members of Human Multigene Familes: Identification and Localisation of UBE2L4, A Novel Member of a Ubiquitin Conjugating Enzyme Dispersed Gene Family" *Cytogenetics and Cell Genetics*, 79:188–192 (1997).
Ambartsumian, N. et al., "Characterization of two splice variants of metastasis–associated human mts1 gene," Gene 159(1): 125–130 (1995).
Bloom, T. J. and Beavo, J. A., "Identification and tissue–specific expression of PDE7 phosphodiesterase splice variants," *Proc. Natl. Acad. Sci. USA* 93(24): 14188–14192 (1996).
Canton, H. et al., "Identification, Molecular Cloning, and Distribution of a Short Variant of the 5–Hydroxytryptamine$_{2C}$ Receptor Produced by Alternative Splicing," *Mol. Pharmacol.* 50(4): 799–807 (1996).
Cheng, J. et al., "Protection from Fas–Mediated Apoptosis by a Solube Form of the Fas Molecule," *Science* 263(5154): 1759–1762 (1994).
Drmanac et al., "Gene–Representing cDNA Clusters Defined by Hybridization of 57,419 Clones from Infant Brain Libraries with Short Oligonucleotide Probes," *Genomics* 37:29–40 (1996).
Ion, A. et al., "a novel Mutation in the Putative DNA Helicase XH2 is Responsible for Male–to–Female Sex Reversal Associated with an Atypical Form of the ATR–X Syndrome," *Am. J. Hum. Genet.* 58(6): 1185–1191 (1996).
Lisitsyn et al., "Comparative genomic analysis of tumors: Detection of DNA losses and amplification," *Proc. Natl. Acad. Sci. USA* 92:151–155 (1995).
Nakajima, T. et al., "A New Alternative Splice Variant of the Mouse FAS Antigen with a Deletion in the N–Terminal Portion of the Extracellular Domain," *Life Sci.* 58(9): 761–768 (1996).
Prashar et al., Analysis of differential gene expression by display of 3' end restriction fragments of cDNAs,*Proc. Natl. Acad. Sci. USA*93:659–663 (1996).
Roemer, K. and Mueller–Lantzsch, N., "p53 transactivation domain mutant Q22, S23 is impaired for repression of promoters and mediation of apoptosis," *Oncogene*12: 2069–2079 (1996).

(List continued on next page.)

*Primary Examiner*—Kenneth R. Horlick
*Assistant Examiner*—Jeffrey Siew
(74) *Attorney, Agent, or Firm*—Clark & Elbing LLP; Kristina Bieker-Brady

(57) ABSTRACT

The present invention is directed to a method for identifying and/or cloning within a biological sample alternatively spliced nucleic acid regions ocurring between two physiological conditions, comprising hybridizing RNA derived from a test condition with cDNA derived from the standard condition and further identifying and/or cloning nucleic acids corresponding to alternative forms of splicing.

25 Claims, 11 Drawing Sheets

OTHER PUBLICATIONS

Roth, J. A. et al., "Retrovirus–mediated wild–type p53 gene transfer to tumors of patients with lung cancer," *Nat. Med.* 2: 985–991 (1996).

Sabbatini, P. et al., "Essential role for p53–mediated transcription in E1A–induced apoptosis," *Genes Dev.* 9:2184–2192 (1995).

Varesco, L. et al., "Mutation in a splice–donor site fo the APC gene in a family with polyposis and late age of colonic cancer death," *Hum. Genet.* 93(3): 281–286 (1994).

Watanabe, K. et al., *J.* "Splicing Isoforms of Rat Ash/Grb2," *Biol. Chem.* 270(23): 13733–13739 (1995).

Zhu, Q. et al., "Deletion within the Src Homology Doman 3 of Bruton's Tyrosine Kinase Resulting in X–linked Agammaglobulinemia (XLA)," *J. Exp. Med.* 180(2): 461–470 (1994).

* cited by examiner path. RNA/normal cDNA hybrids non spliced sequences after RNase H digestion desired sequence which is 5'- and 3'-
labelled by two oligonucléotides PCR-amplified fragment cloning and sequencing

DIFFERENTIAL QUALITATIVE SCREENING

FIELD OF THE INVENTION

The present invention relates to the fields of biotechnology, medicine, biology and biochemistry. Applications thereof are aimed at human health, animal and plant care. More particularly, the invention makes it possible to identify nucleic acid sequences whereby both novel screening tools for identifying molecules of therapeutic interest and novel gene therapy means can be developed. The invention also provides information on molecular toxicity as well as pharmacogenomic data.

The present invention primarily describes a set of original methods for identifying nucleic acid sequences which rely on demonstrating qualitative differences between RNAs derived from two distinct physiological states being compared, in particular those derived from a diseased tissue or organ and healthy equivalents thereof. More precisely, these methods are intended to specifically clone differentially spliced alternative introns and exons with respect to a pathological condition and a healthy state or with respect to two physiological conditions one wishes to compare.

DISCUSSION OF THE PRIOR ART

The characterization of gene expression alterations which underlie, or are linked to a given disorder raises substantial hope regarding the discovery of novel therapeutic targets and of original diagnostic tools. However, identifying a genomic or complementary DNA sequence, whether through positional cloning or quantitative differential screening techniques, yields only little information if at all therefor the function or functional domains involved in regulation defects related to the disease under study.

DETAILED DESCRIPTION OF THE INVENTION

The instant invention describes a set of original methods aimed at identifying differences in splicing occurring between two distinct pathophysiological conditions. Identifying such differences provides information on qualitative but not on quantitative differences as has been the case for techniques described so far. The techniques disclosed in the present invention are hence all encompassed under the term of "qualitative differential screening". The methods of the invention may be used to identify novel targets or therapeutic products, to devise genetic research and/or diagnostic tools, to construct nucleic acid libraries, and to develop methods for determining the toxicological profile or potency of a compound for example.

One particular object of the invention is first to provide a method for identifying alternatively (differentially) spliced nucleic acid regions occurring between two physiological conditions, comprising hybridizing RNAs derived from the test condition with cDNAs originating from a standard condition and identifying nucleic acids which correspond to alternative forms of splicing.

Another object of the invention is to provide a method for cloning differentially spliced nucleic acids occurring between two physiological states, comprising hybridizing RNAs derived from the test condition with cDNAs originating from the standard condition and cloning nucleic acids representative of alternative splicing patterns In a particular embodiment, the method of nucleic acid identification and/or cloning according to the invention comprises running two hybridizations in parallel consisting of:

(a) hybridizing RNAs derived from the test condition with cDNAs derived from the standard condition;
(b) hybridizing RNAs derived from the standard condition with cDNAs derived from the test condition; and
(c) identifying and/or cloning those nucleic acids corresponding to alternative forms of splicing.

The present invention is equally directed to the preparation of nucleic acid libraries, to the nucleic acids and libraries thus prepared, as well as to uses of such materials in all fields of biology/biotechnology, as illustrated hereinafter.

As indicated hereinabove, the present invention relates in particular to methods for identifying and cloning nucleic acids representative of a physiological state. In addition, the nucleic acids identified and/or cloned represent the qualitative characteristics of a given physiological state in that these nucleic acids are generally involved to a great extent in the physiological state being observed. Thus, the qualitative methods of the invention afford direct exploration of genetic elements and protein products thereof, playing a functional role in the development of a pathophysiological state.

The methods of the invention are partly based on an original step consisting of cross hybridization between RNAs and cDNAs belonging to distinct physiological states. This or these cross hybridization procedures allow one to demonstrate in a convenient manner unpaired regions, i.e. regions present in RNAs in one physiological condition and not in RNAs from another physiological condition. Such regions essentially correspond to alternative forms of splicing, typical of a given physiological state, and thus form genetic elements or markers of particular use in the fields of therapeutics and diagnostics as set forth below.

The invention first deals with a method for identifying nucleic acids of interest comprising hybridizing RNAs of a test sample with cDNAs of a standard sample. This hybridization procedure makes it possible to identify the differences in splicing between the conditions under study, and in particular the splicings which are characteristic of the test condition.

According to one variant of the invention, the method allows therefore one to generate a nucleic acid population characteristic of splicing events that occur in a physiological test condition as compared to the standard (reference) condition (FIG. 1A). As indicated hereinafter, this population can be used for the cloning and characterization of nucleic acids, including their use in diagnostics, screening, therapeutics and antibody production or synthesis of whole proteins or protein fragments. This population can also be used to generate libraries that may be used in different application fields as shown hereinafter (FIG. 1C).

According to a further variant of the invention, the method comprises a first hybridization as described hereinbefore and a second hybridization, conducted in parallel, between RNAs derived from a standard condition and cDNAs derived from the test condition. This variant has great advantage since it allows one to generate two nucleic acid populations, one representing the characteristics (qualities) of the test condition with respect to the standard condition, while the other representing the characteristics of the standard condition in relation to the test condition (FIG. 1B). These two populations can be utilized as nucleic acid sources, or as libraries which serve as finger prints of a particular physiological condition, as will be more fully described in the following (FIG. 1C).

The present invention may be applied to all types of biological materials. In particular, the biological material can be any cell, organ, tissue, sample, biopsy material, etc. containing nucleic acids. In case of an organ, tissue or biopsy material, the samples can be cultured so as to facilitate access to the constituent cells. Of interest are samples derived from mammals (especially human beings), plants, bacteria and lower eucaryotic cells (yeasts, fungal cells, etc.). Relevant materials are exemplified in particular by a cancer biopsy, neurodegenerative plaque or cerebral zone biopsy displaying neurodegenerative signs, a skin sample, a blood cell sample obtained by collecting blood, a colorectal biopsy, a bronchial washing biopsy, etc. Examples of cells include muscular cells, hepatic cells, fibroblasts, nervous cells, epidermal and dermal cells, blood cells such as B-, T-lymphocytes, mastocytes, monocytes, granulocytes and macrophages.

As indicated above, the qualitative differential screening according to the invention allows the identification of nucleic acids characteristic of a particular physiological condition (condition B) in relation to a standard (reference) physiological condition (condition A), that are to be cloned or used for other applications. By way of illustration, the physiological conditions A and B being investigated may be chosen among the following:

| Condition A | Condition B |
|---|---|
| Healthy subject-derived sample | Pathological sample |
| Healthy subject-derived sample | Apoptotic sample |
| Healthy subject-derived sample | Sample collected after viral infection |
| X-sensitive sample | X-resistant sample |
| Untreated sample | Treated sample (for example by a toxic compound) |
| Undifferenciated sample | Sample that has undergone cellular or tissue differenciation |

The present invention can be carried out by using total RNAs or messenger RNAs. These RNAs can be prepared by any molecular biology methods, familiar to those skilled in the art. Such methods generally comprise cell, tissue or sample lysis and RNA recovery by means of extraction procedures. This can be done in particular by treatment with chaotropic agents such as guanidinium thiocyanate (which disrupts the cells without affecting RNA) followed by RNA extraction with solvents (phenol, chloroform for instance). The methods listed above are well known in the art (see Maniatis et al., Chomczynski et al., Anal. Biochem., 162 (1987) 156). These methods may be readily implemented by using commercially available kits such as for example US73750 kit (Amersham) for total RNA. RNA need not be used in a fully pure state. In particular, traces of genomic DNA or other cellular components (protein, etc.) remaining in the preparations will not interfere, in as much as they do not significantly affect RNA stability. Optionally, it is further possible to use messenger RNA instead of total RNA preparations. These may be isolated, either directly from biological samples or from total RNAs, by means of polyT chains, according to standard methods. In this respect, the preparation of messenger RNAs can be caried out using commercially available kits such as for example US72700 kit (Amersham). RNAs can also be obtained directly from libraries or other samples prepared beforehand and/or available from collections, stored in suitable conditions.

Generally, the RNA preparations used preferably comprise at least 0.1 $\mu$g of RNA, preferably at least 0.5 $\mu$g of RNA. Quantities can vary depending on the particular cells and methods being used, while keeping the practice of the invention unchanged. In order to obtain sufficient quantities of RNA (preferably at least 0.1 $\mu$g), it is usually recommended to use a biological sample including at least $10^5$ cells. In this respect, a typical biopsy sample generally comprises from $10^5$ to $10^8$ cells, and a cell culture on a typical petri dish (6–10 cm in diameter) contains about $10^6$ cells, so that sufficient quantities of RNA can be readily obtained.

The RNA preparations may be extemporaneously used or stored, preferably in a cold place, as a solution or in the frozen state, for later use.

The cDNA used within the scope of the invention may be obtained by reverse transcription according to conventional molecular biology techniques. Reference is made in particular to Maniatis et al. Reverse transcription is generally carried out using an enzyme, reverse transcriptase, and a primer.

In this respect, many reverse transcriptases have been described in the literature and are commercially available (1483188 kit, Boehringer). Examples of the most commonly employed reverse transcriptases include those derived from avian virus AMV (Avian Myeloblastosis Virus) and from murine leukemia virus MMLV (Moloney Murine Leukemia Virus). It is worth mentioning certain thermostable DNA polymerases having reverse transcriptase activity such as those isolated from *Thermus flavus* and *Thermus thermophilus* HB-8 (commercially available, Promega, catalog number M1941 and M2101). The present invention is conveniently practised using AMV reverse transcriptase since this enzyme, active at 42° C. (in contrast to that of MMLV which is active at 37° C.), destabilizes certain secondary RNA structures that might stop elongation, and therefore allows reverse transcription of RNA of greater length, and provides cDNA preparations in high yields that are much more faithful copies of RNA. The operating conditions that apply to these enzymes (concentration and temperature) are well known to those skilled in the art. In particular, 10 to 30 units of enzyme are generally used in a single reaction, in the presence of an optimal concentration of $Mg^{2++}$ of 10 mM.

The primer(s) used for reverse transcription may be of various types. It might be, in particular, a random oligonucleotide comprising preferably from 4 to 10 nucleotides, advantageously an hexanucleotide. Use of this type of random primer has been described in the literature and allows random initiation of reverse transcription at different sites within the RNA molecules. This technique is especially employed for reverse transcribing total RNA (i.e. comprising mRNA, tRNA and rRNA). Where it is desired to carry out reverse transcription of mRNA only, it might be convenient to use an oligo dT-oligonucleotide as primer, which allows initiation of reverse transcription starting from polyA tails specific to messenger RNAs. The oligo dT-oligonucleotide may comprise from 4 to 20-mers, conveniently about 15-mers. Use of such a primer represents a preferred embodiment of the invention. In addition, il might be convenient to use a labelled primer for reverse transcription. As a matter of fact, this allows recognition and/or selection and/or subsequent sorting of RNA by separation from cDNA. This amy also allow one to isolate RNA/DNA heteroduplex structures the formation of which represents a crucial step in the practice of the invention. Labelling of the primer may be done by any ligand-receptor based system, i.e. providing affinity mediated separation of molecules bearing the primer. It may consist for instance of biotin labelling, which molecule can be captured on any support or substrate (bead, column, plate, etc.) previously coated with streptavidin. Any other labelling system allowing separation without affecting the primer's properties may be likewise utilized.

In typical operating conditions, this reverse transcription generates single stranded complementary DNA (cDNA). This represents a first advantageous embodiment of the present invention.

In a second variant of practising the invention, reverse transcription is accomplished such that double stranded cDNAs are prepared. This result is achieved by generating, following transcription of the first cDNA strand, the second strand using conventional molecular biology procedures involving enzymes capable of modifying DNA such as DNA polymerase I and T4 phage-derived DNA polymerase The DNA preparations may be extemporaneously used or stored, preferably in a cold place, as a solution or in the frozen state, for later use.

As set forth hereinabove, the methods according to the invention are partly based on an original cross hybridization step between RNAs and cDNAs derived from distinct physiological conditions. In a preferred embodiment, hybridization according to the invention is conveniently performed in a liquid phase. Furthermore, it may be carried out in any appropriate device, such as for example tubes (Eppendorf tubes, for instance), plates or any other suitable support that is commonly used in molecular biology. Hybridization is conveniently carried out in volumes ranging from 10 to 1000 $\mu l$, for example from 10 to 500 $\mu l$. It should be understood that the particular device as well as the final volumes used can be easily adapted by those skilled in the field. The choice of nucleic acid amounts for hybridization is equally well known in the art. In general, it is sufficient to use a few micrograms of nucleic acid, for instance in the range of 0.1 to 100 $\mu g$.

An important factor to be considered when performing hybridization is the respective quantities of nucleic acids used. Thus, it is possible to use nucleic acids in a cDNA/RNA ratio ranging from 50 to 0.02 approximately, preferably from 40 to 0.1. In a particularly convenient embodiment, the cDNA/RNA ratio is preferably in the vicinity of 1 or more. Indeed, in such experiments, RNA forms the tester compound and cDNA forms the driver. Accordingly, in order to improve the method's specificity, it is preferred to choose operating conditions where the driver is in excess relative to the tester. In fact, in such conditions, the cooperativity effect between nucleic acids occurs and mismatches are unfavoured to a great extent. As a result, the only mismatches that are observed are generally due to the presence of regions in the tester RNA which are absent from the driver cDNA and which can therefore be considered as specific. In order to enhance specificty of the method, hybridization is conveniently performed using a cDNA/RNA ratio comprised between about 1 and about 10. It will be appreciated that the ratio can be adapted by those skilled in the art depending on the operating conditions (nucleic acid quantities available, physiological conditions, required results, etc.). The other hybridization variables (time, temperature, ionic strength) are also adaptable by those skilled in the art. Generally speaking, after denaturation of the tester and driver (by heating for instance), hybridization is accomplished for about 2 to 24 hours, at a temperature of approximately 37° C. (and by optionally performing temperature shifts as set forth below), and under standard ionic strength conditions (ranging from 0.1 M to 5 M NaCl for instance). It is known that the ionic strength is one factor that defines hybridization stringency, notably in the case of hybridization on a solid support.

According to one specific embodiment of the invention, hybridization is carried out in phenol emulsion, for instance according to the PERT technique (Phenol Emulsion DNA Reassociation Technique) previously described by Kohne D. E. et al., (Biochemistry, vol., 16 N° 24, pp. 5329–5341, 1977). Conveniently, use is made within the scope of the invention of phenol emulsion hybridization under temperature cycling (temperature shifts from about 37° C. to about 60/65° C.) instead of stirring, according to the technique of Miller and Riblet (NAR 23 (1995) 2339). Any other liquid phase-hybridization technique, preferably in emulsion phase, may be used within the scope of the invention.

Hybridization may also be carried out having one of the partners fixed to a support. Conveniently, the cDNA is immobilized. This may be done by taking advantage of cDNA labelling (see hereinabove) especially by using biotin-labelled primers. Biotin moeities are contacted with magnetic beads coated with streptavidin molecules. cDNAs can then be held in contact with the filter or the micro-titer dish well by applying a magnetic field. Under appropriate ionic strength conditions, RNAs are subsequently contacted with cDNAs. Unpaired RNAs are washed away. Hybridized RNAs as well as cDNAs are recovered upon removal of the magnetic field.

Where cDNA is double-stranded, the hybridization conditions used are essentialy similar to those described hereinabove, and adaptable by those skilled in the art. In preference, hybridization is performed in the presence of formamide. In addition, it is desirable to add, following hybridization, a stabilizing agent to stabilize the triplex structures just formed, such as glyoxal for example.

These cross hybridization reactions according to the invention thus generate compositions comprising cDNA/RNA heteroduplex or heterotriplex structures, representing the qualitative properties of each physiological condition being tested. As already noted, in each of the present compositions, nucleic acids essentially corresponding to differential alternative forms of splicing, specific to each physiological condition, can be identified and/or cloned.

In a convenient aspect, the invention relates to a method for identifying and/or cloning within a biological sample differentially spliced nucleic acid regions occurring between two distinct physiological conditions, comprising hybridizing RNAs derived from the test condition with single stranded cDNAs derived from the standard condition, and identifying unpaired RNA regions.

This first variant more specifically rests upon the formation of heteroduplex structures between RNAs and single stranded cDNAs (see FIGS. 2–4). This variant is conveniently implemented using messenger RNAs or cDNAs produced by reverse transcription of essentially messenger RNAs, i.e. in the presence of an oligo dT-primer.

In a particular embodiment, the method for identifying and/or cloning nucleic acids according to the invention comprises:

(a) hybridizing RNAs derived from the test condition with single stranded cDNAs derived from the standard condition;

(b) hybridizing RNAs derived from the standard condition with single stranded cDNAs derived from the test condition; and (c) identifying and/or cloning unpaired RNA regions.

In a particular alternative mode of execution, the method of the invention comprises the following steps:

(a) obtaining RNAs from a biological sample in a physiological condition A (rA);

(b) obtaining RNAs from an identical biological sample in a physiological condition B (rB);

(c) preparing cDNAs from a portion of rA RNAs provided in step (a) (cA DNAs) and from a portion of rB RNAs provided in step (b) (cB DNAs) by means of polyT-primers, (d) hybridizing in a liquid phase a portion of rA RNAs with a portion of cB DNAs (to generate rA/cB heteroduplexes)

(e) hybridizing in a liquid phase a portion of rB RNAs with a portion of cA DNAs (to generate rB/cA heteroduplexes), (f) identifying and/or cloning unpaired RNA regions within the rA/cB and rB/cA heteroduplex structures obtained in steps (d) and (e).

According to an alternative mode of practising the invention, the method of the invention comprises hybridizing RNAs derived from the test condition with double stranded cDNAs derived from the standard condition, and identifying and/or cloning the resulting double stranded DNA regions. This second variant is more specifically based on the formation of heterotriplex structures between RNAs and double stranded cDNAs (see FIG. 5). This variant is equally preferentially practised by using messenger RNA or cDNA produced by reverse transcription of essentially messenger RNA, i.e. in the presence of a polyT primer. In this variant again, a particular embodiment comprises running two hybridizations in parallel, whereby two nucleic acid populations according to the invention are generated. In this variant, the desired regions, specific of alternative splicing events, are not the unpaired RNA regions, but instead double stranded DNA (see FIG. 5).

Starting from nucleic acid populations generated by hybridization, the regions characterizing differential alternative splicing events may be identified by any technique known in the art.

Hence, in case of an RNA/DNA heteroduplex (first variant of this method), these regions essentially appear as unpaired RNA regions (RNA loops), as shown in FIG. 3. These regions may thus be identified and cloned by separating the heteroduplexes and single-stranded nucleic acids (unreacted nucleic acids in excess), selectively digesting the double stranded RNA (portions engaged in heteroduplex structures) and finally separating the resulting single stranded RNA from the single stranded DNA.

In this respect, according to a first approach illustrated in FIG. 3, the unpaired RNA regions are identified by treatment of heteroduplexes by means of an enzyme capable of selectively digesting the RNA domains engaged in RNA/DNA heteroduplexes. Enzymes having such activity are known from the prior art and are commercially available. It can be mentioned RN-ases H, such as in particular, those derived from *E. coli* by recombinant techniques and commercially available (Promega, catalog number M4281; Life Technologies, catalog number 18021). This first treatment thus generates a mixture comprising unpaired single stranded RNA regions and single stranded cDNA. The RNAs may be separated from cDNAs by any procedure known in the art, such as, for instance, on the basis of labelling of those primers used to prepare cDNA (see above). These RNAs can be used as a source of material for identifying targets, gene products of interest or for any other relevant application. These RNAs can be equally converted into cDNA, and then cloned into vectors, as described hereinafter.

In this regard, cloning RNAs may be done in different ways. One way is to insert at each RNA end oligonucleotides acting as templates for a given reverse transcription reaction in the presence of compatible primers. Primers may be appended according to techniques well known to those skilled in the art by means of an enzyme, such as for example RNA ligase derived from the T4 phage and which catalyzes intermolecular phosphodiester bond formation between a 5' phosphate group of a donor molecule and a 3' hydroxyl group of an acceptor molecule. Such an RNA ligase is commercially available (for example from Life Technologies—GIBCO BRL, catalog number 18003). cDNA thus obtained may then be amplified by conventional techniques (PCR for example) using the appropriate primers, as illustrated in FIG. 3 and in the following examples. This technique is especially adapted to cloning short RNA molecules (less than 1000 bases).

Another approach for cloning and/or identifying specific RNA regions involves for example a reverse transcription reaction, performed either upon heteroduplexes directly generated by hybridization, or upon the digests of an enzyme acting specifically on double stranded RNA, using random primers, which will randomly initiate transcription along RNAs. cDNAs thus obtained are then amplified according to conventional molecular biology techniques, for example by PCR using primers formed by appending oligonucleotides to cDNA ends by means of T4 phage DNA ligase (commercially available: for example from Life Technologies—GIBCO BRL, Cat. No. 15224). This second technique is illustrated in FIG. 4 and fully described in the examples. Such a technique is especially adapted to long RNA, and provides a sufficient part of the sequence data to subsequently reconstruct the whole intial sequence.

In general, the identification and/or cloning step of RNA is based on these two methods so as to generate as much information as possible.

In case of heterotriplex structures (another variant of this method), these differentially spliced regions are in the form of double stranded DNA, as represented in FIG. 5. Such regions may thus be identified and cloned by treating them by means of appropriate enzymes such as an enzyme capable of digesting the RNA, and next by an enzyme capable of digesting single stranded DNA. The nucleic acids are thus directly obtained in the form of double stranded DNA and could be cloned inside any suitable vector.

The vectors used in the invention are plasmids, cosmids, phages, YAC, HAC, etc. These nucleic acids may be stored as such, or introduced into micro-organisms compatible with the cloning vector being used, for replication and/or stored in the form of cultures.

The time interval required for carrying out the methods herein described for each sample is generally less than two months, in particular less than 6 weeks. Furthermore, these different methods may be automated so that the total length of time is reduced and treatment of a big number of samples is simplified.

In this regard, another object of the invention concerns nucleic acids that have been identified and/or cloned by the methods of the invention. As already noted, these nucleic acids may be RNAs or cDNAs. More generally, the invention concerns a nucleic acid composition, essentially comprising nucleic acids corresponding to alternative splicings which are distinctive of two physiological conditions. More particularly, these nucleic acids correspond to alternative splicings identified in a biological test sample and not present in the same biological sample under a standard (reference) condition. The invention is equally concerned with the use of the nucleic acids thus cloned as therapeutic or diagnostic products, or as screening tools to identify active molecules, as set forth hereinafter.

The different methods disclosed hereinabove thus all lead to the cloning of cDNA sequences representative of differentially spliced genetic information between two pathophysiological conditions. The whole set of clones derived from these methods makes it thus possible to construct a library representative of qualitative differences occurring between two conditions of interest.

In this respect, the invention is further directed to a method for preparing nucleic acid libraries representative of a given physiological state of a corresponding biological sample. This method conveniently comprises cloning nucleic acids representative of alternative forms of splicing of said physiological state but not present in a standard condition, to generate libraries specific to qualitative differences existing between the two conditions being investigated.

These libraries are constituted by cDNA inserted in plasmid or phage vectors. Such libraries can be overlaid (coated) on nitrocellulose filters or any other support known to those skilled in the art, such as chips or biochips.

One of the features as well as one of the original characteristics of qualitative differential splicing is that this technique does not lead only to one but instead two differential libraries which represent the whole set of qualitative differences occurring between two given conditions thus obtaining a library pair (cf. FIG. 1C).

The choice of initial RNAs will partly determine the characterstics of the resulting libraries:

RNAs of both conditions A and B are mRNAs or total mature RNAs isolated according to techniques known to those skilled in the art. The libraries are thus so-called restricted qualitative differential screening libraries, since they are restricted to qualitative differences that characterize the mature RNA of both physiological conditions.

the RNAs of one of either conditions are mRNAs or mature total RNAs whereas the RNAs of the other condition are premessenger RNAs, not processed by splicing, isolated according to techniques known to those skilled in the art, from cellular nuclei. In that situation, the resulting libraries are so-called complex differential screening libraries, as being not restricted to differences between mature RNAs but rather comprising the whole set of spliced transcripts in a given condition which are absent from the other, including all introns.

finally, the RNAs could arise from a single pathophysiological condition and in this case the differential screening involves mature RNA and premessenger RNA of the same sample. In such a case, the resulting libraries are autologous qualitative differential screening libraries. The usefulness of such libraries lies in that they include the whole range of introns transcribed in a given condition. Whether they hybridize or not with a probe derived from mature RNAs of a distinct condition allows one to quickly ascertain if the condition under study is characterized by persisting introns while providing for their easy identification.

Preferably, the library is constructed by cross hybridizing RNA arising from the physiological condition being tested with cDNA derived from the standard physiological condition and selecting nucleic acids of interest by proceeding as previously described. In addition, once such libraries are constructed, it is possible to proceed with a step of clone selection to improve the specificity of the resulting libraries. Indeed, it may be that certain mismatches observed are not solely due to differential alternative splicing patterns, but result from reverse transcription defects for example. Although such events are not generally significant, it is preferable to prevent them or reduce their incidence prior to nucleic acid cloning. To achieve this result, the library clones may be hybridized with the cDNA populations occurring in both physiological conditions being investigated (see step (c) hereinabove). The clones effectively hybridizing with both populations would be considered as non specific and optionally discarded. The clones which do hybridize with only one out of two populations are considered as specific and could be selected to construct refined or enriched libraries.

A refining step may be equally performed by hybridizing and checking the identity of clones by means of probes derived from a statistically relevant number of pathological samples.

The present application is further directed to any nucleic acid library comprising nucleic acids specific of alternative forms of splicing typical of a physiological condition. These libraries conveniently comprise cDNAs, generally of double stranded nature, corresponding to RNA regions specific of alternative splicing. Such libraries may be comprised of nucleic acids, generally incorporarated within a cloning vector, or of cell cultures containing said nucleic acids.

Generally speaking, the libraries are generated by spreading, on a solid medium (notably on agar medium), of a cell culture transformed by the cloned nucleic acids. Transformation is done by any technique known to those skilled in the art (transfection, calcium phospahate precipitation, electroporation, infection with bacteriophage, etc.). The cell culture is generally a bacterial culture, such as for example *E. coli*. It may also be a eucaryotic cell culture, such as lower eucaryotic cells (yeasts for example). This spreading step can be performed in sterile conditions on a dish or any other suitable support. Additionally, the spread cultures in agar medium can be stored in a frozen state for example (in glycerol or any other suitable agent). Naturally, these libraries can be used to produce "duplicates", i.e. copies made according to common techniques more fully described hereinafter. Furthermore, such libraries are generally used to prepare an amplified library, i.e. a library comprising each clone in an amplified state. An amplified library is prepared as follows: starting from a spread culture, all cellular clones are recovered and packed for storage in the frozen state or in a cold place, using any compatible medium. This amplified library is conveniently prepared from *E. coli* bacterial cultures, and is stored at 4° C., in sterile conditions. This amplified library allows preparation and illimited replication of any subsquently prepared library containing such clones, on individual supports, for a variety of applications. Such a library further allows the isolation and characterization of any clone of interest. Each clone composing the libraries of the invention is indeed a characteristic element of a physiological condition, and constitutes therefore a very interesting target for various studies such as the search for markers, antibody production, diagnostics, gene transfer therapy. These different applications are discussed in more detail below. The library is generally prepared as described above by spreading the cultures in an agar medium, on a suitable support (petri dish for example). The advantage of using an agar medium is that each colony can be separated and distinctly recognized. Starting from this culture, identical duplicates may be prepared in substantial amounts simply by replica-plating (lifting) on any suitable support according to techniques known in the art. Thus, the duplicate may be obtained by means of filters, membranes (nylon, nitrocellulose, etc.) on which cell adhesion is possible. Filters may then be stored as such, at 4° C. for example, in a dried state, in any other packing medium that does not alter nucleic acids. Filters may be equally treated in such a manner as to discard cells, proteins, etc., and to retain only such components as nucleic acids. These treatment procedures may notably comprise the use of proteases, detergents, etc. Treated filters may be equally stored in any device or under any condition acceptable for nucleic acids.

The nucleic acid libraries could be equally directly prepared from nucleic acids, by transfer onto biochips or any other suitable device.

The invention is further directed to any support material (membrane, filter, biochip, chip, etc) comprising a library as defined hereinabove. This may be in particular a cell library or a nucleic acid library. The invention also includes any kit or support material comprising several libraries according to the invention. In particular, it may prove convenient to use a library representative of the qualitative features of a test physiological condition with respect to a standard physiological condition and, as control, a library representative of the features of a standard physiological condition in relation to the test physiological condition (a library pair). A convenient kit according to the invention hence comprises two differential qualitative libraries belonging to two physiological conditions ("a library pair"). According to one particular embodiment, the kits persuant to the invention comprise several library pairs as defined hereinabove, corresponding to distinct physiological states or to different biological samples for example. Such kits may comprise for example different library pairs serially arranged on a common support.

The invention is yet further directed to any library comprising oligonucleotides specific of alternative splicing events that distinguish two physiological conditions. It may convenienlty be single stranded oligonucleotides comprising from 5 to 100-mer, in preference less than 50 -mer, for example in the range of 25-mer.

These oligonucleotides are specific of alternative splicings representative of a given condition or type of physiological condition. Thus, such oligonucleotides may for example be oligonucleotides representative of alternative splicing events characteristic of apoptotic states. Indeed, it has been reported in the literature that certain alternative splicing events are observed in apoptotic conditions. This holds especially true for splicing within Bclx, Bax, Fas or Grb2 genes for example. By referring to published data or sequences available in data base systems, it is possible to generate oligonucleotides specific to is spliced or unspliced forms. These oligonucleotides may for example be generated according to the following strategy:

(a) identifying a protein or a particular splicing event characteristic of an apoptotic condition and the sequence of the spliced domain. This identification procedure can be based upon published data or a compilation of available sequences in data base systems;

(b) synthesizing artificially one or more oligonucleotides corresponding to one or more regions of this domain, which therefore allow the identification of the unspliced form in the RNAs of a test sample through hybridization;

(c) synthesizing in vitro of one or more oligonucleotides corresponding to the junction region between two domains spaced apart by the spliced portion. These oligonucleotides allow the identification of the spliced form in the RNAs of a test sample through hybridization;

(d) repeating steps (a) to (c) listed above with other proteins or splicing events characteristic of apoptotic conditions;

(e) transferring upon a first suitable support material one or a plurality of oligonucleotides specific to apoptotic forms of messengers identified hereinabove and, to another suitable support, one or a plurality of oligonucleotides specific to non apoptotic forms.

The two supports thus obtained may be used to assess the physiological state of cells or test samples, including the apoptotic condition, through hybridization of a nucleic acid preparation derived from such cells or samples.

Other similar libraries can be generated using oligonucleotides specific to distinct pathophysiological states (neurodegeneration, toxicity, proliferation, etc.) thus broadening the application range. Alternative intron or exon libraries can also be in the form of computerized data base systems compiled by systematically analyzing data bases in which information about genomes of individual organisms, tissues or cell cultures are recorded. In such a case, the data obtained by elaboration of such virtual data bases may be used to generate oligonucleotide primers that will serve in testing two pathophysiological conditions in parallel.

The computerized data bases may further be used to derive versatile nucleotide probes, representative of a given class of proteins, or specific of a particular sequence. These probes can then be overlaid (deposited) on the clone libraries derived from different alternative intron and exon cloning techniques in order to appreciate the complexity of these molecular libraries and rapidly determine whether a given class of protein or a given defined sequence is differentially spliced when comparing two distinct pathophysiological states.

The method of the invention thus provides for the systematic identification of qualitative differences in gene expression. These methods have many applications, related to the identification and/or cloning of molecules of interest, in the fields of toxicology, pharmacology or still, in pharmacogenomics for example.

The invention is therefore additionally concerned with the use of the methods, nucleic acids or libraries previously described for identifying molecules of therapeutic or diagnostic value. The invention is more specifically concerned with the use of the methods, nucleic acids or libraries described hereinabove for identifying proteins or protein domains that are altered in such a pathology.

One of the major strengths of these techniques is, indeed, the identification, within a messenger, and consequently within the corresponding protein, of the functional domains which are affected in a particular disorder. This makes it possible to assess the importance of a given domain in the development and persistence of a pathological state. A direct advantage of restricting to a given protein domain the impact of a pathological disorder resides in that the latter can be viewed as a relevant target for screening small molecules for therapeutic purposes. These information further constitute a key for designing therapeutically active polypeptides that may be delivered by gene therapy; such polypeptides can namely be single chain-antibodies derived from neutralizing antibodies against domains identified by techniques herein described.

More specifically, the methods according the invention provide molecules which:

may be coding sequences derived from alternative exons.

may correspond to non coding sequences born by introns differentially spliced between two pathophysiological states.

From the foregoing data, different information can be obtained.

Alternative splicings of exons which discriminate between two pathophysiological states reflect a regulatory mechanism of gene expression capable of modulating (in more precise terms suppress or restore) one or a number of functions of a particular protein. Therefore, as the majority of structural and functional domains (SH2, SH3, PTB, PDZ and catalytic domains of various enzymes) are encoded by several contiguous exons, two configurations might be considered:

i) the domains are truncated in the pathological condition (Zhu, Q. et al., 1994, *J. Exp. Med.*, vol: 180, n° 2n pp. 461–470); this indicates that the signalling pathways involving such domains must be restored for therapeutical purposes.

ii) the domains are retained in the course of a pathological disorder whereas they are absent from the healthy state; these domains must be considered as screening targets for compounds of low molecular weight intended to antagonize signal transduction mediated by such domains.

The differentially spliced sequences may correspond to non coding regions located 5' or 3' of the coding sequence or to introns occurring between two coding exons. In the non coding regions, these differential splicings could reflect a modification of the messenger stability or translatability. (Bloom, T. J. et Beavo, J. A. 1995, Proc. Natl. Acad. Sci USA, vol 93, n° 24, pp. 14188–14192; Ambartsumian N. et al. 1995, Gene, vol. 159, n° 1, pp. 125–130). A search for these phenomena should be conducted based on such information and might qualify the corresponding protein as a candidate target in view of its accumulation or disappearance. Retention of an intron in a coding sequence often results in the truncation of the native protein by introducing a stop codon within the reading frame (Varesco, L., et al., 1994, Hum. Genet., vol. 93, n° 3, pp. 281–286; Canton, H. et al., 1996, Mol. Pharmacol., vol. 50, n° 4, pp. 799–807, Ion, A., et al., 1996, Am. J. Hum. Genet., vol. 58, n° 6, pp. 1185–1191). Before such a stop codon is read, there generally occurs translation of a number of additional codons whereby a specific sequence is appended to the translated portion which behaves as a protein marker of alternative splicing. These additional amino acids can be used to produce antibodies specific to the alternative form inherent to the pathological condition. These antibodies may subsequently be used as diagnostic tools. The truncated protein undergoes a change or even an alteration in properties. Thus enzymes may loose their catalytic or regulatory domain, becoming inactive or constitutively activated. Adaptors may lose their capacity to link different partners of a signal transduction cascade (Watanabe, K. et al., 1995, J. Biol. Chem., vol. 270 n° 23, pp. 13733–13739). Splicing products of receptors may lead to the formation of receptors having lost their ability to bind corresponding ligands (Nakajima, T. et al., 1996, Life Sci., vol. 58, n° 9, pp. 761–768) and may also generate soluble forms of receptor by release of their extracellular domain (Cheng. J., 1994, Science, vol 263, n° 5154, pp. 1759–1762). In this case, diagnostic tests can be designed, based on the presence of circulating soluble forms of receptor which bind a given ligand in various physiological fluids.

The invention is more specifically concerned with the use of the methods, nucleic acids or libraries described hereinabove for identifying antigenic domains that are specific for proteins involved in a given disorder. The invention is equally directed to the use of the nucleic acids, proteins or peptides as described above for diagnosing pathological conditions.

The invention is equally directed to a method for identifying proteins or protein domains involved in a pathological process comprising:

(a) hybridizing messenger RNAs of a pathological sample with cDNAs of a healthy sample, (b) identifying splicing forms which are specific to the pathological state in relation to the healthy state, (c) identifying protein or protein domains corresponding to one or several splicing forms identified in step (b).

The protein(s) or protein domains may be isolated, sequenced, and used in therapeutic or diagnostic applications, including antibody production.

To better illustrate this point, the qualitative differential screening of the invention allows one to conveniently identify tumor suppressor genes. Indeed, many examples indicate that one way suppressor genes are inactivated in the course of tumoral progression is inactivation by modulation of alternative forms of splicing.

Hence, in small cell lung carcinoma, the gene of protein p130 belonging to the RB family (retinoblastoma protein) is mutated at a consensus splicing site. This mutation results in the removal of exon 2 and in the absence of synthesis of the protein due the presence of a premature stop codon. This observation was the first of its kind to underline the importance of RB family members in tumorigenesis. Likewise, in certain non small cell lung cancers, the gene of protein p16INK4A, a protein which is an inhibitor of cyclin-dependant kinase cdk4 and cdk6, is mutated at a donnor splicing site. This mutation results in the production of a truncated short half-life protein that is accompanied, which lead to the accumulation of inactive phosphorylated forms of RB. Furthermore, WT1, the Wilm's tumor suppressor gene, is transcribed into several messenger RNAs generated by alternative splicings. In breast cancers, the relative proportions of different variants are modified in comparison to healthy tissue, hence yielding diagnostic tools or hints in understanding the importance of the various functional domains of WT1 in tumoral progression. The same alteration process affecting ratios between different messenger RNA forms and protein isoforms during cellular transformation is again found in case of neurofibrin NF1. In addition, the concept that modulation of splicing phenomena behaves as a marker of tumoral progression is supported by the HDM2 example where five alternative splicing events are detected in ovarian and pancreatic carcinoma, the expression of which increases depending on the cancer developmental stage. Furthermore, in head and neck cancer, one of the mechanisms by which p53 is inactivated involves a mutation at a consensus splicing site.

These few examples clearly illustrate the interest of the methods of the invention based on screening for alternative splicing patterns which discriminate between a given tumor and an adjacent healthy tissue. Results thus obtained allow not only the characterization of known tumor suppressor genes but also, in view of the original and systematic aspect of qualitative differential screening methods, the identification of novel alternative splicings specific to tumors that are likely to affect new tumor suppressor genes.

The invention is thus further directed to the identification of tumor suppressor genes or splicing events occurring within those tumor suppressor genes, as previously defined. This method may conveniently comprise the following steps of:

(a) hybridizing messenger RNAs of a tumoral sample with cDNAs of a healthy sample, (b) identifying splicing events specific to the tumoral sample in relation to the healthy sample, (c) identifying protein or protein domains corresponding to one or more splicing events identified in step (b).

The tumor suppressor properties of proteins or protein domains identified may then be tested in different known models. These proteins, or their native forms (displaying a splicing pattern in the healthy tissue), may then be used for various therapeutic or diagnostic applications, including antitumoral gene therapy.

The present application therefore relates not only to different aspects of embodying the present technology but also to the exploitation of the resulting information in research, development of screening assays for chemical compounds of low molecular weight, and development of gene therapy or diagonstic tools.

In this connection, the invention is concerned with the use of the methods, nucleic acids or libraries described above in genotoxicology, i.e. to predict the toxicity of test compounds.

The genetic programs initiated during treatment of cells or tissues by toxic agents are predominantly correlated with apoptotic processes or programmed cellular death. The importance of alternative splicing processes in regulating such apoptotic mechanisms is well described in the literature. However, no single gene engineering technique described to date allows full screening and isolation of sequence variations due to alternative splicings distinctive of two pathophysiological conditions. The qualitative differential splicing screening methods developed by the present invention make it possible to gather all splicing differences occurring between two conditions within cDNAs libraries. Comparing RNA sequences (for example messenger RNAs) of a tissue (or of a cell culture) either treated or not by a standard toxic compound allows the generation of cDNA libraries which comprise gene expression qualitative differences characterizing the toxic effect being investigated. These cDNA libraries may then be hybridized with probes derived from RNA arising from the same tissues or cells treated with the chemical being assessed for toxicity. The relative capacity of these probes to hybridize with the genetic sequences specific to a given standard toxic condition allows toxicity of the compound to be determined.

Toxicity determination may be performed more specifically following two approaches:

According to a first approach, the qualitative differential screening may be accomplished between a standard tissue or cell culture not subjected to treatment on the one hand, and treated by the product whose toxicity is to be assessed on the other hand. The analysis of clones representative of specifically induced qualitative differences as a result of this product subsequently provides for the detection within these clones of events closely related to cDNA involved in toxic reactions such as apoptosis.

Such markers are monitored as they arise as a function of the dosage regimen and duration of treatment by the product in question so that the toxicological profile thereof may be established.

The present invention is further directed to a method for identifying, by means of qualitative differential screening according to the methods set forth above, toxicity markers induced in a model biological system by a chemical compound whose toxicity is to be measured. In this connection, the invention relates in particular to a method for determining or assessing the toxicity of a test compound upon a particular biological sample comprising preparing a library pair of the sample either subjected or not to treatment by the test compound, and searching for toxicity markers in the library specific to the post-treatment sample properties.

According to the second approach, abacus are prepared for different classes of toxic products, that are fully representative of the toxicity profiles as a function of dosage and treatment duration for a given standard tissue or cell model. For each abacus dot, cDNA libraries which are wholly representative of alternative splicing events can be generated. The latter represent differential libraries: they are obtained by subtracting genetic information from the dot selected in the abacus diagram and from the corresponding dot in the standard tissue ou cell model. As set forth in the examples, the qualitative differential screening is based on hybridizing mRNA derived from a particular condition with cDNAs derived from another condition. As already noted, the differential screening may also be conducted using total RNAs or nuclear RNAs containing premessenger species.

In this respect, the invention deals with a method for determining or assessing the toxicity of a test compound to a given biological sample comprising hybridizing:

libraries of the invention characteristic of said biological sample from a healthy state and at various stages of toxicity resulting from treatment of said sample with a standard toxic compound, with, a nucleic acid preparation of the biological sample treated by said test compound, and determining the toxicity of the test compound by determining the extent of hybridization with the different libraries.

According to this method, it is convenient to proceed with two cross hybridizations for each condition (compound dosage):

RNAs from condition A and cDNAs from condition B (rA/cB)

RNAs from condition B and cDNAs from condition A (rB/cA)

To each standard toxic condition, or each abacus dot, there are assigned two qualitative differential screening libraries. One of such libraries is a full collection of qualitative differences, i.e. the alternative splicing events specific to the normal standard condition whereas the other library is a full collection of splicing events specific to the toxic situations. These libraries are replica-plated on solid support materials such as nylon or nitrocellulose filters or more conveniently on chips. The libraries initially formed of cDNA fragments of variable length (according to the splicing events being considered) may be optimized by using oligonucleotides derived from previously isolated sequences.

Where a chemical compound is a candidate for pharmaceutical development, this may be tested with the same tissue or cell models as those recorded in the toxicity abacus-like diagram. Molecular probes may then be synthesized from mRNA extracts of biological samples treated by the chemical compound of interest. These probes are then hybridized on filters bearing cDNA of rA/cB and rB/cA libraries. For instance, rA/cB library may contain sequences specific to the normal condition and rB/cA library may contain alternative spliced species specific to the toxic condition. Innocuity or toxicity of the chemical compound is then readily assessed by looking at the hybridization profile of an mRNA extract-derived probe belonging to the standard tissue or cell model that has been treated by the test compound; namely:

efficient hybridization with the rA/cB library and no signal in the rB/cA library demonstrates the compound has no toxicity on the model under study a positive hybridization reaction between the probe and the rB/cA library clones is an evidence of a test compound-induced toxicity Practical applications related to such libraries may be provided by the hepatocyte culture models, such as the HepG2 line, following treatment by toxic agents such as ethanol.

A preferred example may be provided by use in cosmetic testing of skin culture models subjected or not to treatment by toxic agents or irritants.

A yet another object of the present application is therefore differential screening libraries made from standard organ, tissue or cell cultures treated by chemical compounds representative of broad classes of toxic agents according to abacus charts disclosed in the literature. The invention further encompasses the spreading of these libraries on filters or support materials known to those skilled in the art (nitrocellulose, nylon . . . ). Conveniently, these support materials may be chips which hence define genotoxicty chips. The invention is further concerned with the potential exploitation of the sequencing data about different clones making up these libraries in order to understand the mechanisms underlying the effects of various toxic agents, as well as with the use of such libraries in hybridization with probes derived from cells or tissues treated by a chemical compound or a pharmaceutical product the toxicity of which is to be determined. Conveniently, the invention relates to nucleic acid libraries such as of the type defined above, prepared from skin cells treated under different toxic conditions. The invention is further concerned with a kit comprising the aforementioned individual skin differential libraries.

The invention is yet further directed to the use of methods, nucleic acids or libraries previously described to assess (predict) or enhance the therapeutic effectiveness of test compounds (genopharmacology).

In this particular use, the underlying principle is very similar to that previously described. The two standard libraries are established from a control cell culture or organ and counterparts thereof simulating a pathological model. The therapeutic efficiency of a given product may then by evaluated by monitoring its potential to antagonize gene expression qualitative variations which are specific of the pathological model being considered. This is demontrated by a change in the hybridization profile of a probe derived from the pathological model with the standard libraries, otherwise stated, in the absence of treatment, the probe only hybridizes with the library containing the specific splicing markers of the disease. Following treatment with the efficient product, the probe, though it is derived from the pathological model, hybridizes preferentially with the other library, which bears the markers of the healthy model equivalent.

In this connection, the invention is further directed to a method for determining or assessing the therapeutic efficiency of a test compound upon a given biological sample comprising hybridizing:

libraries according to the invention typical of said biological sample in a healthy state and in a disease state (at different developemental stages), with a preparation of nucleic acids originating from the biological sample treated by said test compound, and assessing the therapeutic potential of the test compound by determining to what extent hybridization occurs with the individual libraries prepared.

Such an application is exemplified by an apoptotic model simulating certain aspects of neurodegeneration which are antagonized by standard trophic factors. Thus, cells derived from the PC12 pheochromocytome line which are differentiated into neurites in the presence of NGF will soon undergo apoptosis upon removal of this growth factor. This apoptotic process is accompanied by expression of many programmed cell death markers, several of which are regulated by alternative splicing and downregulated by IGF-1. Two libraries derived from qualitative differential screening are established from mRNA extracts of differenciated PC12 cells in the process of apoptosis following NGF removal on one hand and from differenciated PC12 cells prevented from undergoing apoptosis by supplementing IGF-1 on the other hand. To these libraries, may be hybridized probes prepared from differenciated PC12 mRNA extracts in the process of apoptosis the survival of which is enhanced by treatment with a neuroprotective product to be tested. The efficiency of the test compound to reverse the qualitative characteristics can thus be appreciated by monitoring the capacity of the probe to selectively hybridize to those specific library clones representing cells having a better survival rate. This test could be subsequently used to test the efficiency of derivatives of such a compound or any other novel family of neuroprotective compounds and to improve the pharmacological profile thereof.

In a specific embodiment, the method of the invention allows one to assess the efficiency of a neuroprotective test compound by carrying out hybridization with a differential library according to the invention derived from a healthy nervous cell and a neurodegenerative model cell In a further embodiment, one is interested in testing an anti-cancer compound using differential libraries established from tumoral and healthy sample cells.

As already noted, the method of the invention could furthermore be used to improve the properties of a compound, by testing the capacity of various derivatives thereof to induce a hybridization profile similar to that of the healthy sample representative library.

The invention is still further directed to the use of the methods, nucleic acids or libraries described hereinabove in pharmacogenomics, i.e., to assess (predict) the response of a patient to a given test compound or treatment.

Pharmacogenomics is aimed at establishing genetic profiles of patients with a view to determine which treatment would reasonably be successful for a given pathology. The procedures described in the present invention make it possible in this connection to establish cDNA libraries that are representative of qualitative differences occurring between a pathological condition which is responsive to a given treatment and another condition which is unresponsive or poorly responsive thereto, and thus may qualify for a different therapeutic strategy. Once these standard libraries are established, they can be hybridized with probes prepared from the patients' messenger RNAs. The hybridization results allow one to determine which patient has a hybridization profile corresponding to the responsive or non responsive condition and thus refine treatment choice in patient management.

In the present practical application, the purpose is on one hand to suggest depending on the patient history the most appropriate treatment regimen most likely to be successful and on another hand to enroll in a given treatment regimen those patients which are most likely to benefit therefrom. As with other applications, two qualitative differential screening libraries are prepared: one based on a pathological model or sample known to respond to a given treatment, and another based on a further pathological model or sample which is poorly responsive or unresponsive to therapy. These two libraries are then hybridized with probes arising from mRNAs extracted from biopsy tissues of individual patients. Depending on whether such probes preferentially hybridize with the alternatively spliced forms specific to one particular condition, the patients may be divided into responsive and unresponsive subjects to the standard treatment which initially served to define the models.

In this respect, the invention is also directed to a method for determining or assessing the response of a particular patient to a test compound or treatment comprising hybridizing:

a library characteristic of a responsive biological sample to said compound/treatment and a library characteristic of an unresponsive or poorly responsive biological sample to said compound/treatment, with, a nucleic acid preparation of a pathological biological sample of the patient, and assessing the responsiveness of the patient by determining the extent of hybridization with those different libraries.

The usefulness of qualitative differential screening in pharmacogenomics is illustrated for instance by a qualitative differential screening between two tumors of the same histological origin, one of which showing regression by treatment with an antitumoral compound (for example transfer of cDNA coding for wild-type p53 protein by gene therapy), while the other being unresponsive to such treatment. The first benefit derived from constructing qualitative differential libraries between these two conditions is the ability to determin, by analyzing clones making up these libraries, which molecular mechanisms are elicited during regression as observed in the first model and rather inactive in the second.

Subsequently, the use of filters or any other support material bearing cDNAs derived from these libraries allows one to conduct hybridization with probes derived from mRNAs of tumoral tissue-biopsies the response of which to such treatment is to be predicted. It is possible by looking at the results to assign patients to an optimized treatment regimen.

One particular example of this method consists of determining the tumor response to p53 tumor suppressor gene therapy. It has indeed been reported that certain patients and certain tumors respond more or less to this type of treatment (Roth et al., Nature Medicine, 2 (1996), 985). It is therefore essential to determine which types of tumors and/or which patients are sensitive to wild-type p53 gene therapy, in order to optimize treatment and make the best choice regarding the enrollment of patient in clinical trials being undertaken. Conveniently, the method of the invention makes it possible to simplify the procedure by providing libraries specific to qualitative characteristics of p53-responsive cells and non responsive cells. Examples of cell models sensitive or resistant to p53 are described for instance by Sabbatini et al. (Genes Dev., 9 (1995) 2184) or by Roemer et al. (Oncogene, 12 (1996), 2069). Hybridization of these libraries with biopsy samples-derived probes will make assessment of patient responsiveness easier. In addition, the specific libraries will allow identification of nucleic acids involved in p53 gene-responsiveness.

The present application is therefore also directed to the establishment of differential screening libraries from pathological samples, or pathological models, which vary in responsiveness to at least one pharmacological agent. These libraries could be restricted, complex or autologous libraries as defined supra. It is also concerned with the spreading of these libraries upon filters or support materials known to those skilled in the art (nitrocellulose, nylon . . . ). In a convenient manner, these support materials may be chips which thus define pharmacogenomic chips. The invention further relates to the potential exploitation of sequencing data of different clones forming such libraries in order to thoroughly understarid the mechanisms which lead pathological samples to respond differently to various treatments, as well as to the use of such libraries for conducting hybridization with probes derived from biopsy tissue originating from pathological conditions one wishes to predict the response to the standard treatment initially used to define those libraries.

Other advantages and practical applications of the present invention will become more apparent from the following examples which are given for purposes of illustration and not by way of limitation.

EXAMPLES

1. DIFFERENTIAL CLONING OF ALTERNATIVE SPLICINGS USING SINGLE STANDED cDNA

Figure 1A:
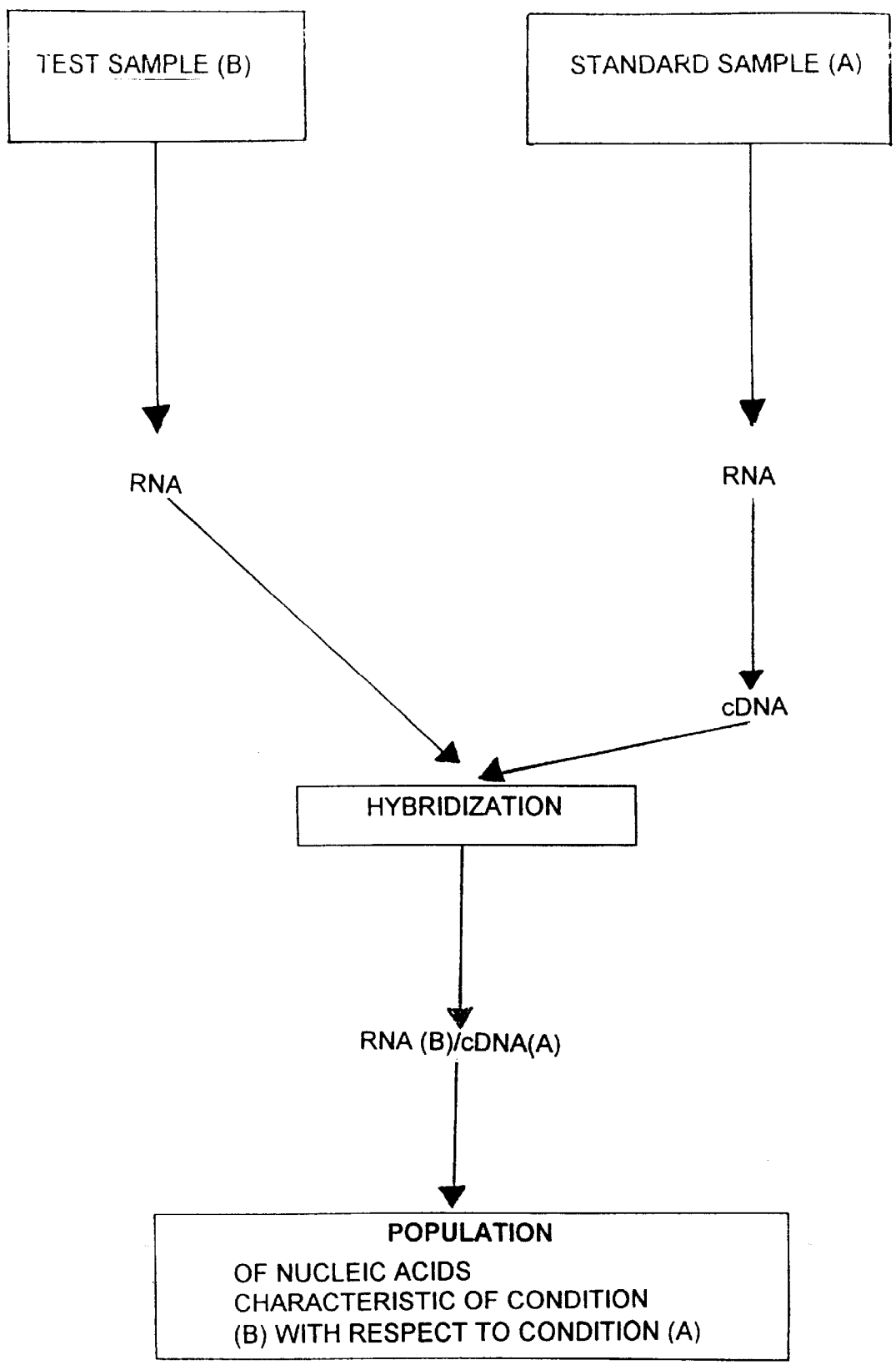
FIGS. 1A–C schematically represent differential screening assays according to the invention using one (FIG. 1A) or two (FIG. 1B) hybridization procedures, and practical applications of nucleic acids therefrom (FIG. 1C).
Figure 1B:
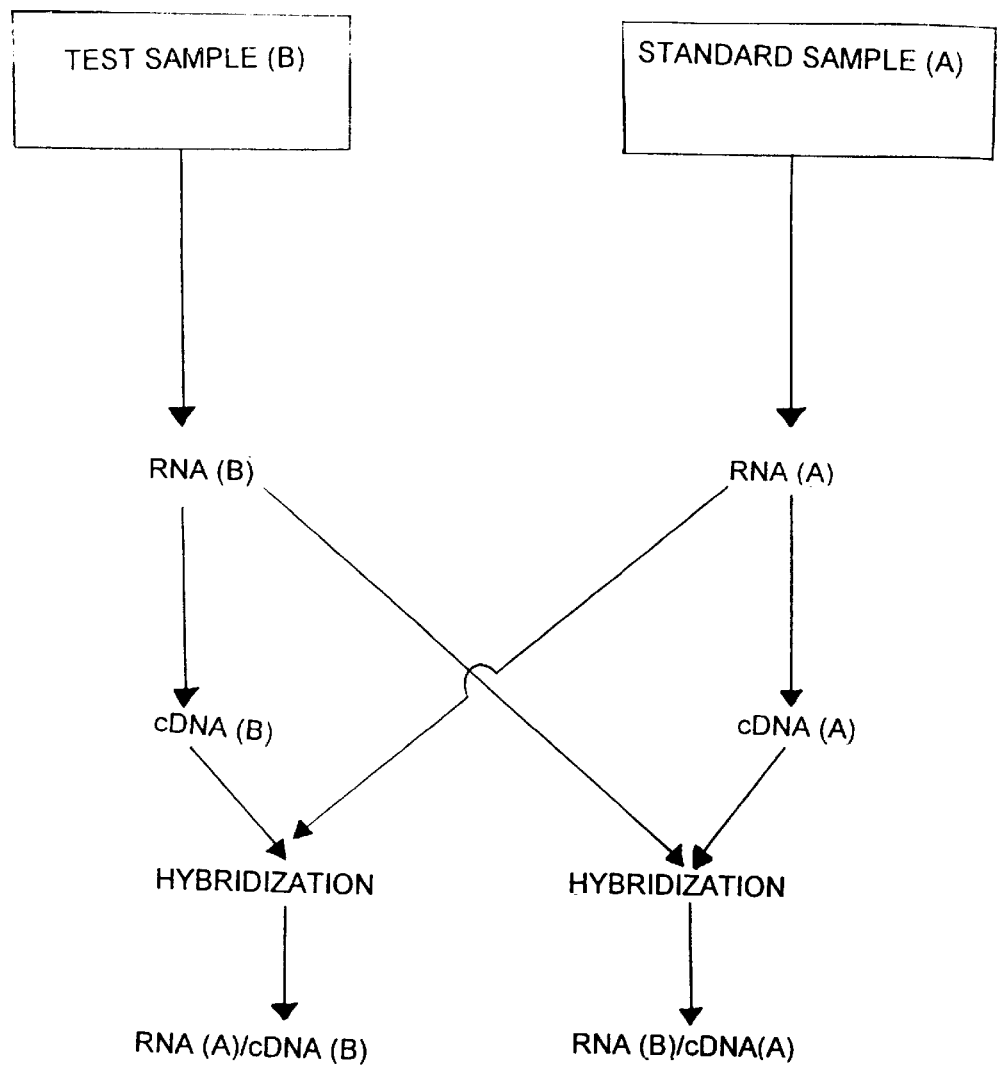
Figure 1C:
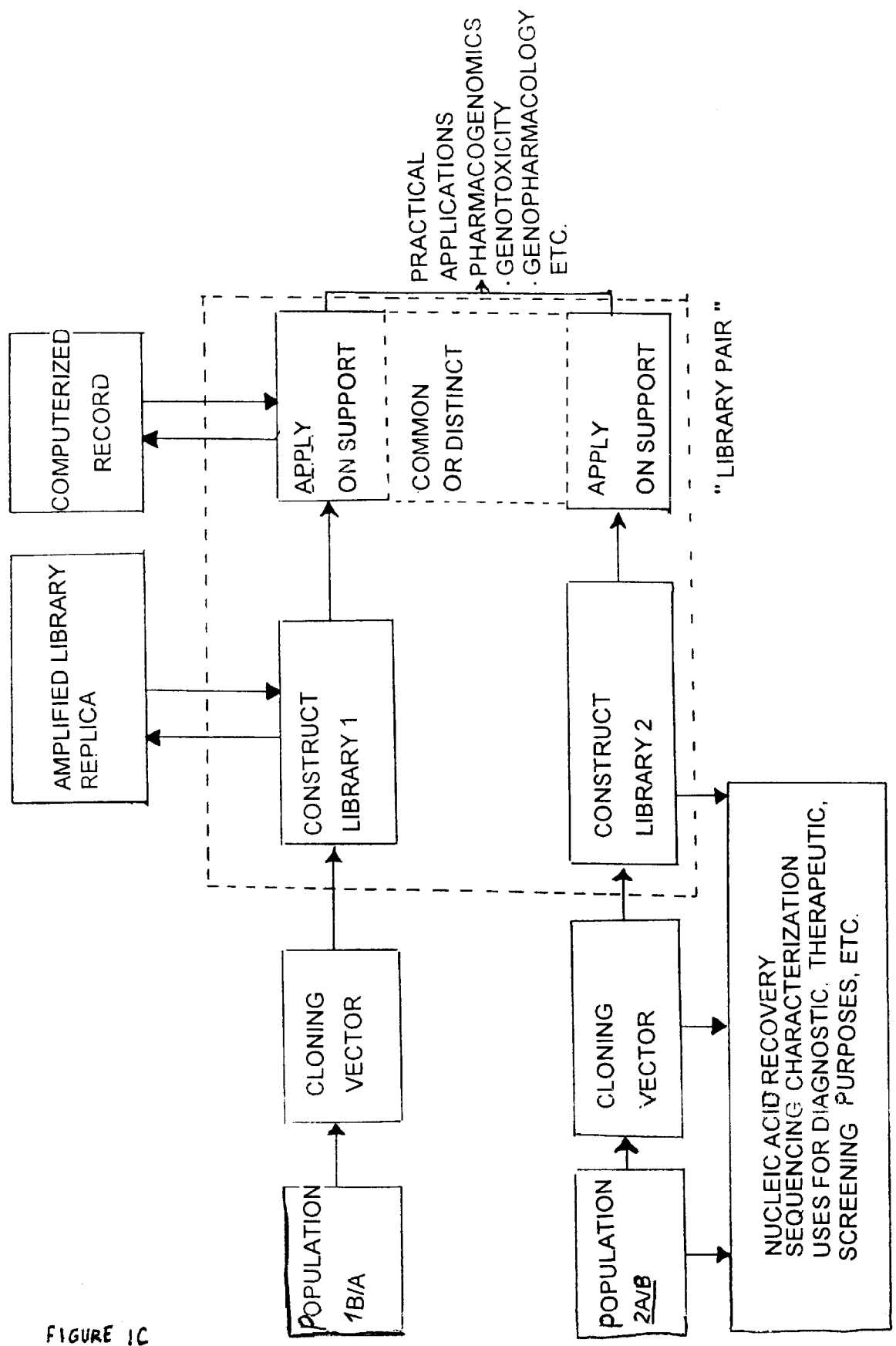
Figure 2:
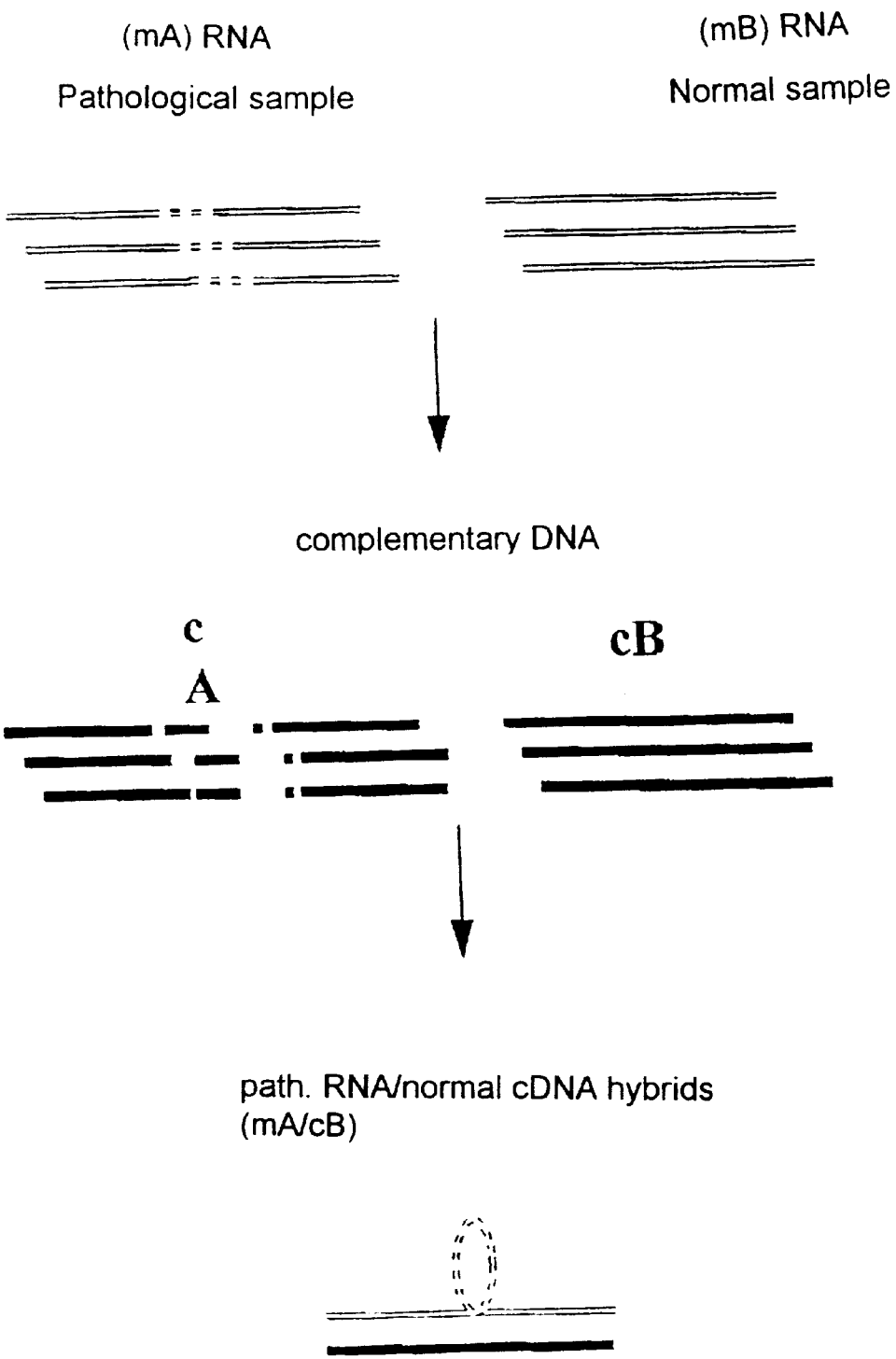
FIG. 2 schematically represents the production of RNA/DNA hybrids allowing single stranded RNA sequences to be characterized, the former being specific markers of the pathological and healthy state.
Figure 3:
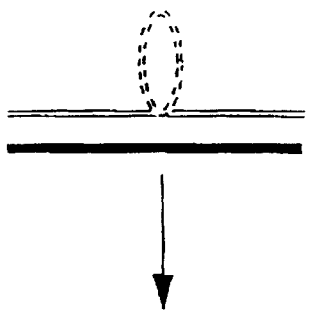
FIG. 3 schematically represents a method for isolating and characterizing by sequencing single stranded RNA sequences specific to a given pathological or healthy condition.
Figure 3:
Figure 3:
Figure 3:

Messenger RNAs corresponding to two conditions, one being normal (mN) and the other being of a pathological origin (mP), are isolated from biopsy samples or cultured cells. These messenger RNA are converted into complementary DNAs (cN) and (cP) by means of reverse transcriptase (RT). mN/cP and cN/mP hybrids are then prepared in a liquid phase (see the diagram of FIG. 2 illustrating one of either cases leading to the formation of cN/mP). These hybrids are conveniently prepared in phenol emulsion (PERT technique or Phenol Emulsion DNA Reassociation Technique) constantly subjected to thermocycling (Miller, R., D., and Riblet, R., 1995, Nucleic Acids Research, vol. 23, n° 12, pp. 2339–2340). Typically, this hybridization step is executed using between 0.1 and 1 $\mu$g of polyA+ RNA and 0.1 to 2 $\mu$g of complementary DNA in an emulsion formed of an aquous phase (120 mM sodium phosphate buffer, 2.5 M NaCl, 10 mM EDTA) and an organic phase representing 8% of the aqueous phase and formed of twice distilled phenol. There is obtained as a result an RNA/DNA heteroduplex the base pairing extent of which depends on the ability of RT to synthesize the entire cDNA. Other single stranded structures observed are RNA (and DNA) regions corresponding to alternative splicings which distinguish the two pathophysiological states under study. The method is aimed at characterizing the genetic information born by such splice loops. To achieve this result, several experimental alternatives may be considered:

A. A first approach consists in isolating and cloning such loops (FIG. 3).

The RNA/DNA heteroduplex structures are digested by RN-ase H which will degrade RNA hybridized to DNA according to procedures known to those skilled in the art. The products of this hydrolysis are on the one hand DNA and, on the other hand, RNA fragments which correspond to splice loops or non hybridized regions as a result of incomplete RT reaction. These fragments are separated from DNA by conventional techniques, with RT primers being optionally biotinylated for example. One then proceeds with ligation of oligonucleotides to each RNA end by means of RNA ligase according to conditions known in the art. These oligonucleotides are then used as primers to effect RT PCR. The PCR products are cloned and screened with total complementary DNA probes corresponding to the two pathophyisological conditions of interest. Only those clones preferentially hybridizing with one of either probes contain the splice loops which are finally sequenced.

Figure 4:
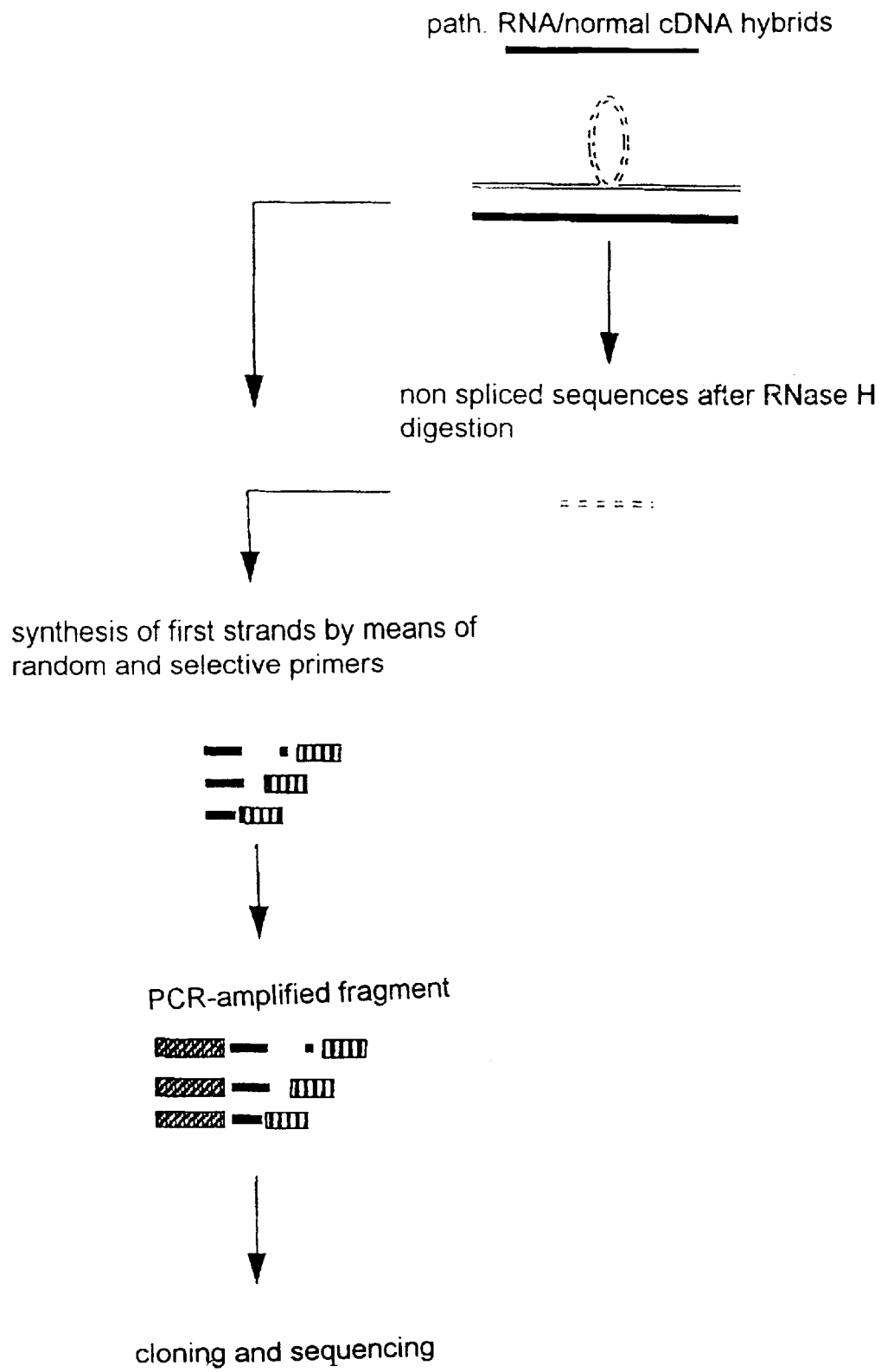
FIG. 4 schematically represents another means for characterizing by sequencing all or part of the single stranded-RNAs specific to a given pathological or healthy condition.

B. The second approach (FIG. 4) consists in reacting RT with heteroduplexes that have been previously purified thanks to the biotinylated DNA primers, or with single stranded RNA that have been released by RNase H cleavage, as set forth above. This RT is primed by means of primers formed of random 3' hexanucleotides and of a determined 5' sequence. The primers may therefore hybridize anywhere along the single stranded RNA. A second strand is then synthesized in a random fashion as well. PCR is run using primers corresponding to specific sequences of 5' and 3' ends in order to obtain splice loopsderived sequences.

These two examples allow the production of nucleic acid compositions representing the differential splicings in both conditions being tested.

Figure 5:
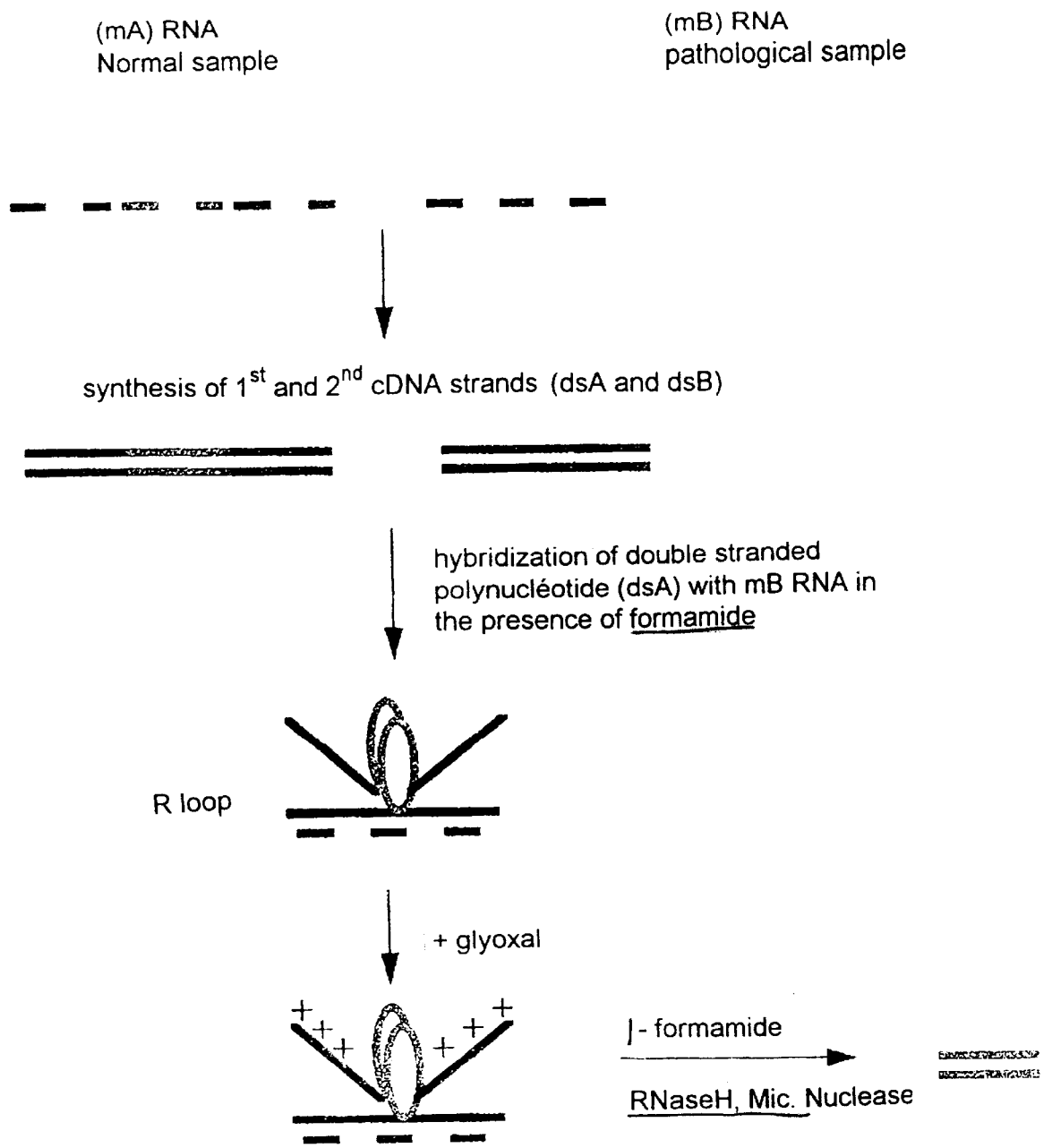
FIG. 5 schematically represents the isolation of alternatively spliced products based on R-loop structures.
Figure 6:
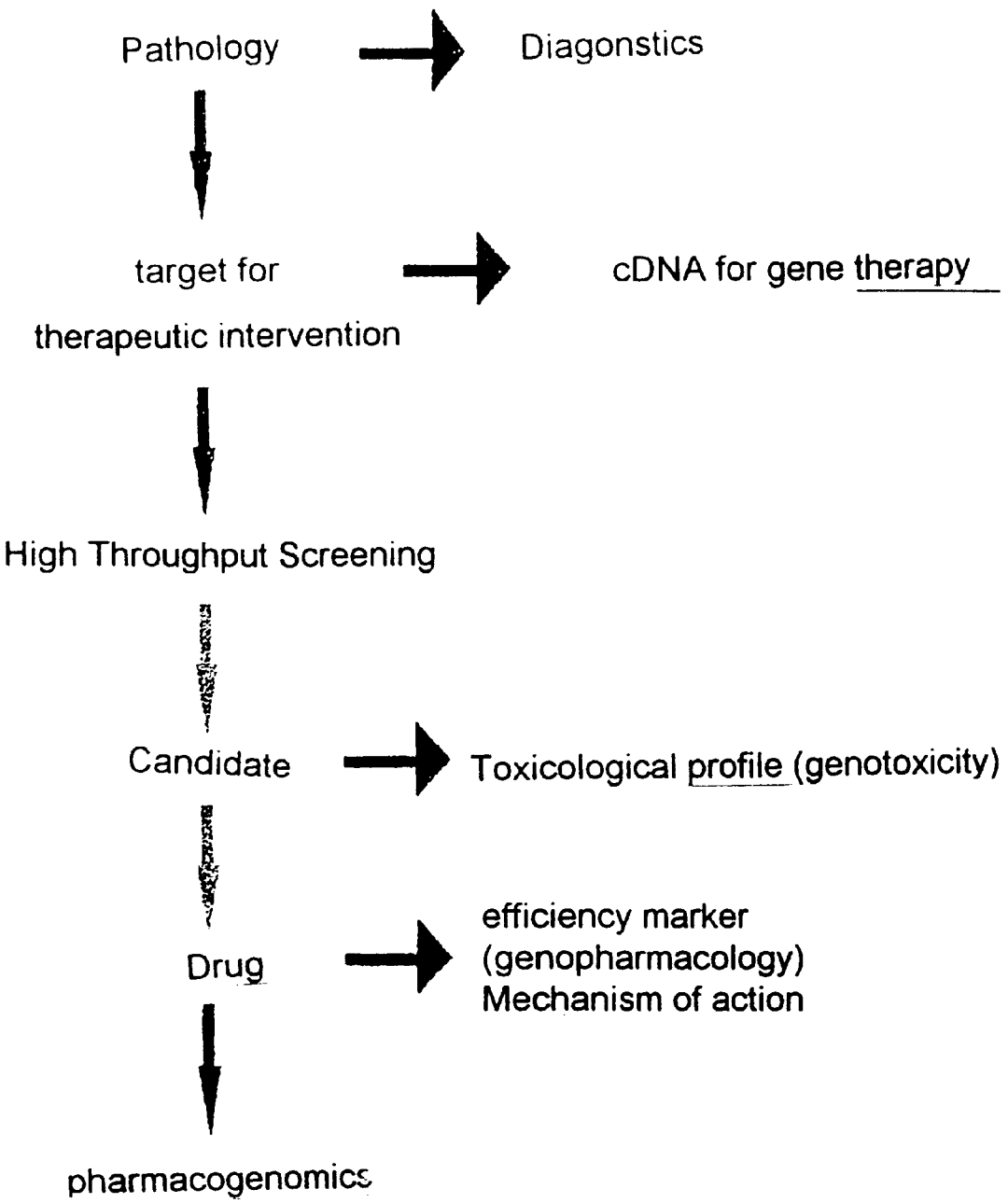
FIG. 6 outlines the benefits of qualitative differential screening to pharmaceutical research at various stages of development.
Figure 7:
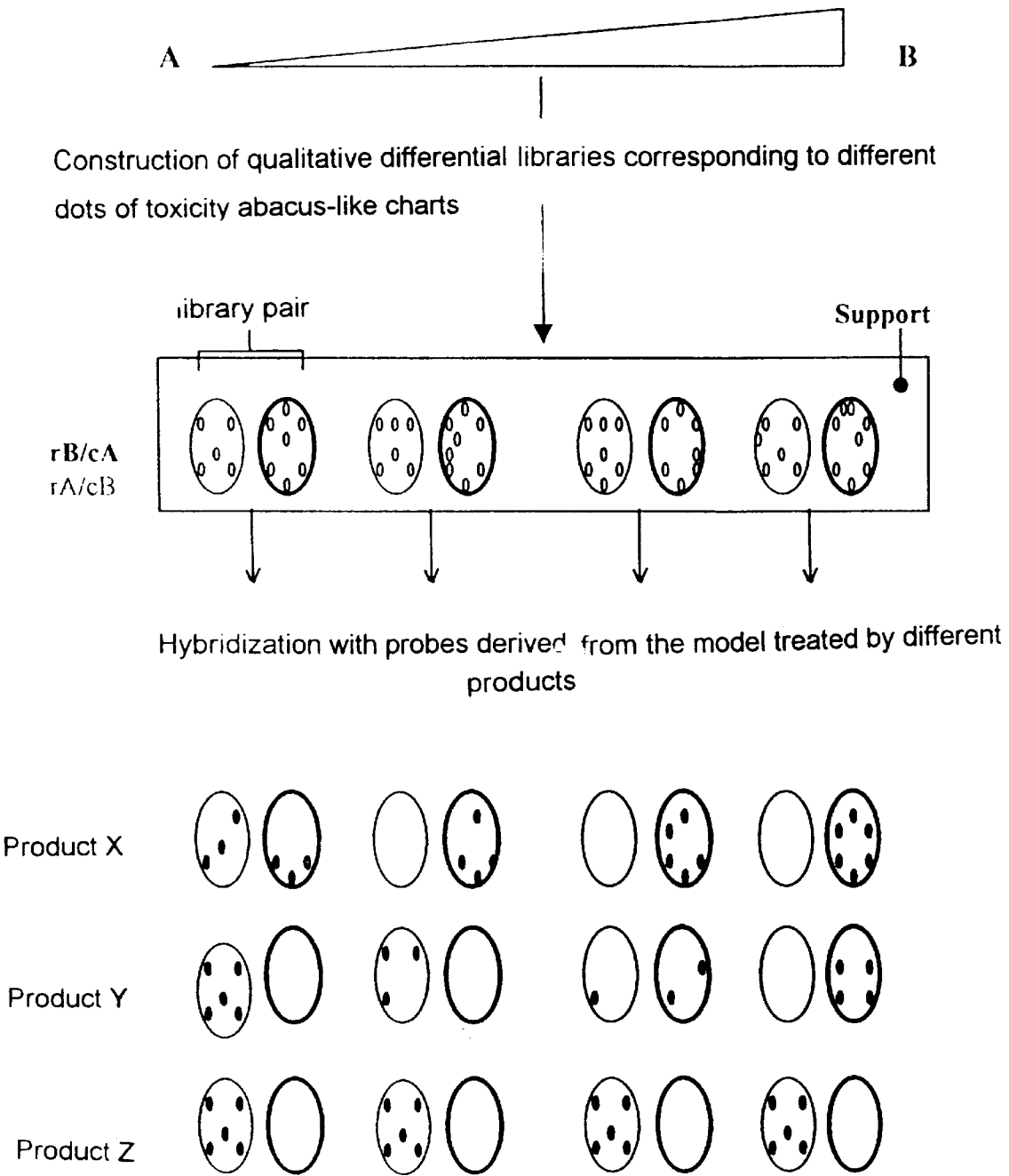
FIG. 7 Experimental procedure for assessing the toxicity of a product.

2. DIFFERENTIAL CLONING OF ALTERNATIVE SPLICINGS USING DOUBLE STRANDED cDNA (FIG. 5)

Messenger RNAs corresponding to normal (mN) and pathological (mP) conditions are produced, as well as corresponding double stranded complementary DNAs (dsN and dsP) by standard molecular biology procedures. R-loop structures are then obtained by hybridizing respectively mN with dsP and mP with dsN in a solution containing 70% of formamide. Differentially spliced nucleic acid domains between conditions N and P will remain in the form of double stranded DNA. Displaced single stranded DNAs are then treated with glyoxal to avoid further displacement of the RNA strand upon removal of formamide. After removal of formamide and glyoxal and treatment with RNaseH, there are obtained bee-type structures, the unpaired single stranded DNAs being representative of the bee wings and the paired double stranded domain of interest being reminescent of the bee's body. The use of a mutant micrococcal nuclease specific to single stranded DNAs allows the isolation of DNA in double stranded form, which is next cloned and sequenced. This second technique allows for direct formation of double stranded DNA fingerprints of the domain of interest, when compared to the first procedure which yields RNA fingerprints.

3. CONSTRUCTION OF LIBRARIES DERIVED FROM QUALITATIVE DIFFERENTIAL SCREENING

The two examples described hereinabove lead to the cloning of cDNAs representative of all or part of differentially spliced sequences as observed between two pathophysiological conditions. These cDNAs allow the construction of libraries by insertion of such cDNAs into plasmid or phage vectors. These libraries may be overlaid on nitrocellulose filters or any other support material known in the art, such as chips or biochips or membranes. The aforementioned libraries may be stored in a cold place, away from light. These libraries, once applied (deposited) and fixed on support materials by conventional techniques, may be treated by cell disruptive compounds.

One of the features as well as one the original characteristics of qualitative differential screening is that this method conveniently leads to not only one but two differential libraries ("library pair") which represent the whole array of qualitative differences occurring between two given conditions. In particular, one of the differential splicing libraries represents the unique qualitative markers of the test physiological condition as compared to the standard physiological condition, while the latter represents the unique qualitative markers of the physiological condition in relation to the test physiological condition. This couple of libraries is equally termed a library pair or "differential splicing library".

4. USES AND BENEFITS OF QUALITATIVE DIFFERENTIAL LIBRARIES

The potential applications of differential splicing libraries of the invention are notably illustrated on FIGS. 6 to 9. Thus, these libraries are useful for:

4.1. Evaluating the Toxicity of a Compound (FIG. 7):

In this example, the standard condition is designated A and the toxic condition is designated B. Toxicity abacus charts are obtained by treating condition A in the presence of various concentrations of a standard toxic compound, for different periods of time. For different dots of toxicity abacus charts, qualitative differential libraries are constructed (library pairs), namely in this example, restricted libraries rA/cB and rB/cA. The library pairs are conveniently overlaid on a support. The support is then hybridized with probes derived from the original biological sample, treated by different concentrations of test compounds: Products X, Y, Z. The hybridization reaction is developped in order to determine the toxicity power of the test products: in this example, product Z is highly toxic and product Y shows an intermdiate profile.

Figure 8:
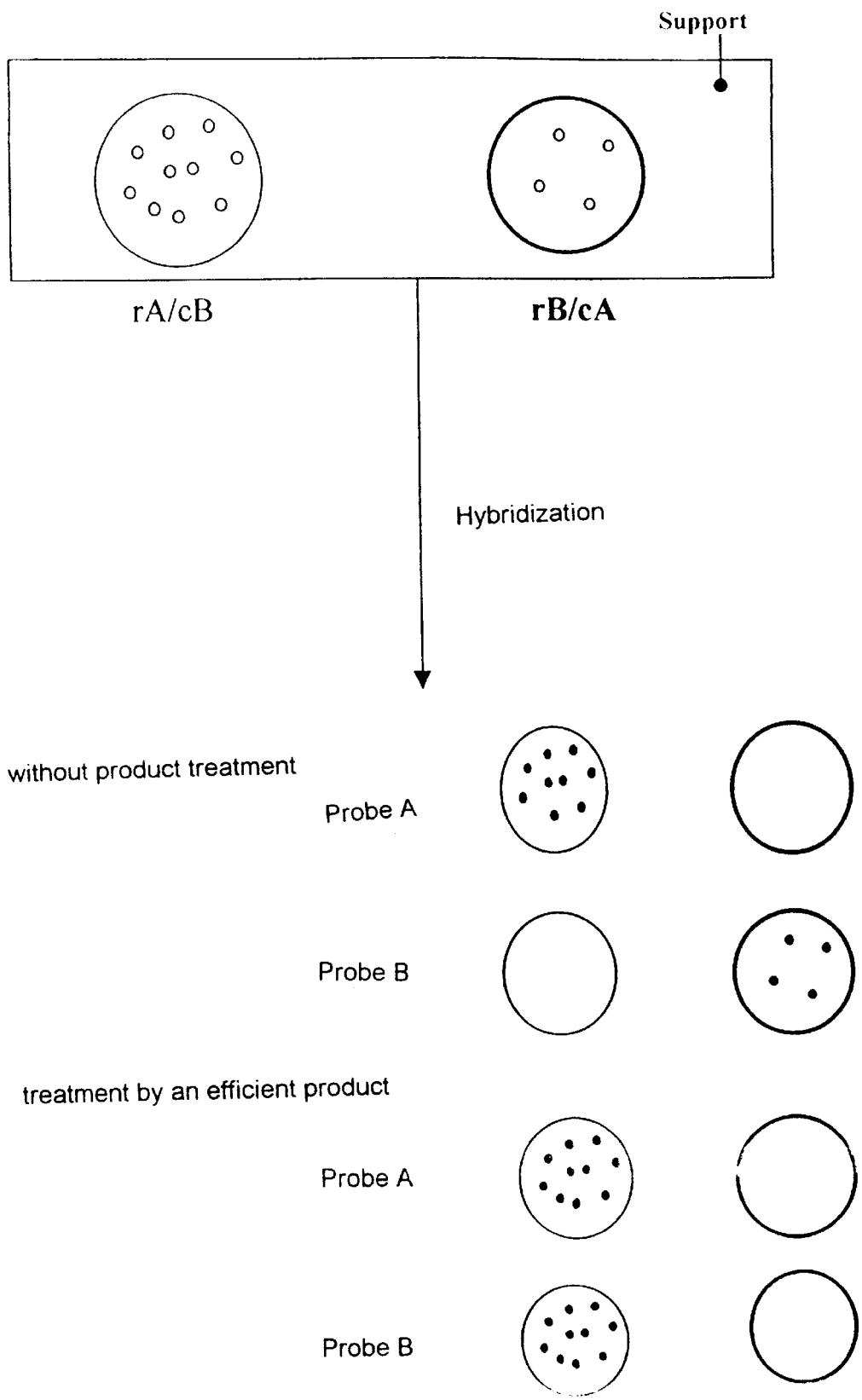
FIG. 8 Experimental procedure for monitoring the efficiency of a product.
Figure 9:
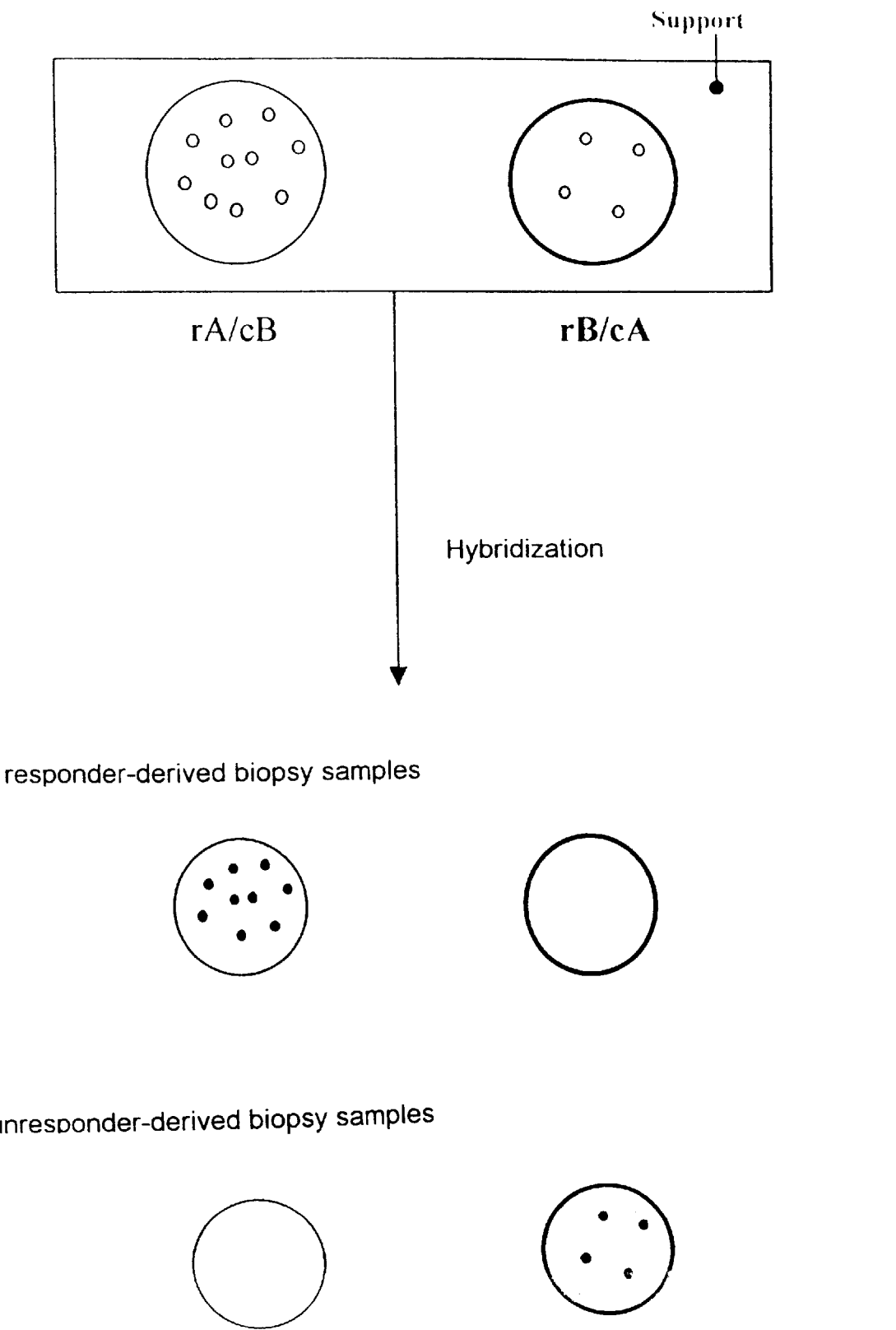
FIG. 9 Experimental procedure for investigating the sensitivity of a pathological condition to a given treatment.

4.2. Assessing the Potency of a Pharmaceutical Composition (FIG. 8):

In this example, a restricted library pair according to the invention is constructed starting with a pathological model B and a healthy model A (or a pathological model treated with a standard active product). The differential libraries rA/cB and rB/cA are optionally overlaid on a substrate. This library pair is fully representative of the differences in splicing which occur between both conditions. This library pair allows the efficiency of a test compound to be assessed, i.e. to determine its capacity to generate a healthy-like profile (rA/cB) starting from a pathological-type profile (rB/cA). In the present example, the library pair is hybridized with probes prepared from conditions A and B either under treatment or not by the test compound. The hybridization profile is shown in FIG. 8.

4.3. Predicting the Response of a Pathological Sample to a Given Treatment (FIG. 9):

In this example, a restricted library pair according to the invention is constructed starting with two pathological models, one of which is responsive to treatment by a given product (the wild-type p53 gene): condition A; while the other being unresponsive: condition B. This library pair (rA/cB; rB:CA) is arranged on a support.

This library pair is then used to determine the sensitivity of a pathological test sample to the same product. For that purpose, the library pair is hybridized with probes derived from patients' biopsy tissues one wishes to evaluate the response to standard treatment. The hybridization profile of a responsive subject biopsy sample and of an unresponsive subject biopsy sample is presented on FIG. 9.

As is apparent from the above description, the invention is further concerned with:

any nucleic acid probe, any oligonucleotide, any antibody which recognizes a sequence identified by the method described in the present application and characterized in that they are characteristic of a pathological condition, the use of information derived from applying the techniques disclosed herein for the search of organic molecules for therapeutic purposes by devising screening assays characterized in that they target differentially spliced domains occurring between a healthy and a pathological condition or else characterized in that they are based on the inhibition of functions acquired by the protein as a result of differential splicing, the utilization of the information derived from the methods described in the present specification for gene therapy applications, the use of cDNAS delivered by gene therapy, wherein said cDNAS behave as antagonists or agonists of defined cell signal transduction pathways, any construction or use of molecular library of alternative exons or introns for purposes of:
  commercial production of diagnostic means or reagents for research purposes
  generation or search of molecules, polypeptides, nucleic acids for therapeutical applications.

construction or use of all computerized virtual libraries containing an array of alternative exons or introns characterized in that said libraries allow the design of nucleic acid probes or oligonucleotide primers in order to characterize alternative splicing forms which distinguish two different pathophysiological conditions.

any pharmaceutical or diagnostic composition comprising polypeptides, sense or antisense nucleic acids or chemicals capable of interfering with alternative splicing products identified and cloned by the methods of the invention, any pharmaceutical or diagnostic composition comprising polypeptides, sense or antisense nucleic acids, or molecules capable of restoring a splicing pattern representative of a normal condition in contrast to an alternative splicing event inherent to a pathological condition.

What is claimed is:

1. A method for identifying or cloning nucleic acids comprising sequences corresponding to portions of genes that are differentially spliced between two biological samples containing nucleic acids, wherein the composition or sequence of the nucleic acids in said biological samples is at least partially unknown, said method comprising:
   a) hybridizing a plurality of different RNAs derived from a first sample, wherein the composition or sequence of the RNAs is at least partially unknown, with a plurality of different cDNAs derived from a second sample, wherein the composition or sequence of the cDNAs is at least partially unknown; and
   b) identifying or cloning, from the hybrids formed in a), a population of nucleic acids comprising an unpaired region, said cloned or identified nucleic acids comprising an unpaired region corresponding to portions of genes that are differentially spliced between said samples.

2. A method for identifying or cloning nucleic acids comprising sequences corresponding to portions of genes that are differentially spliced between two biological samples containing nucleic acids, wherein the composition or sequence of the nucleic acids in said biological samples is at least partially unknown, wherein said method comprises:
   a) hybridizing a plurality of different RNAs derived from a first sample, wherein the composition or sequence of the RNAs is at least partially unknown, with a plurality of different cDNAs derived from a second sample, wherein the composition or sequence of the cDNAs is at least partially unknown, on one hand;
   b) hybridizing a plurality of different RNAs derived from the second sample, wherein the composition or sequence of the RNAs is at least partially unknown, with a plurality of different cDNAs derived from the first sample, wherein the composition or sequence of the cDNAs is at least partially unknown, on the other hand; and
   c) identifying or cloning, from the hybrids formed in (a) and (b), nucleic acids comprising an unpaired region, at least a portion of said cloned or identified nucleic acids comprising an unpaired region corresponding to said differentially spliced nucleic acids from said genes.

3. A method according to claim 1 or 2, wherein said cDNAs are single stranded cDNAs and said identifying or cloning in step (b) of claim 1 or step (c) of claim 2 comprises identifying or cloning unpaired RNA regions.

4. A method according to claim 1 or 2, wherein said cDNAs are double stranded cDNAs and said identifying or cloning in step (b) of claim 1 or step (c) of claim 2 comprises identifying or cloning paired DNA regions.

5. A method according to claim 1 or 2, wherein said first or second sample comprises a cell, a tissue, an organ, or a biopsy sample.

6. A method according to claim 1 or 2, wherein one of said samples is from tumoral cells and the other of said samples is from non-tumoral cells.

7. A method according to claim 1 or 2, wherein one of said samples is from cells treated by a test compound and the other of said samples is from untreated cells.

8. A method according to claim 1 or 2, wherein one of said samples is from cells undergoing apoptosis and the other of said samples is from non-apoptotic cells.

9. A method according to claim 1 or 2, wherein said hybridization is performed in a liquid phase.

10. A method for identifying or cloning nucleic acids distinct of two biological samples containing nucleic acids, wherein the composition or sequence of the nucleic acids in said biological samples is at least partially unknown, said method comprising:
    a) generating heteroduplex structures in a liquid phase between a plurality of different messenger RNAs derived from a first sample, wherein the composition or sequence of the RNAs is at least partially unknown, and a plurality of different cDNAs derived from a second sample, wherein the composition or sequence of the cDNAs is at least partially unknown, on one hand;

b) generating heteroduplex structures in a liquid phase between a plurality of different messenger RNAs derived from the second sample, wherein the composition or sequence of the RNAs is at least partially unknown, and a plurality of different cDNAs derived from the first sample, wherein the composition or sequence of the cDNAs is at least partially unknown, on the other hand; and c) identifying or cloning at least one unpaired RNA region within heteroduplex structures from steps (a) and (b), said cloned or identified unpaired RNA region corresponding to a nucleic acid distinct of said samples.

11. A method for identifying or cloning nucleic acids distinct of two biological samples containing nucleic acids, wherein the composition or sequence of the nucleic acids in said biological samples is at least partially unknown, said method comprising:

a) generating heteroduplex structures between a plurality of different messenger RNAs derived from a first sample, wherein the composition or sequence of the RNAs is at least partially unknown, and a plurality of different cDNAs derived from a second sample, wherein the composition or sequence of the cDNAs is at least partially unknown, on one hand, the RNAs or cDNAs being fixed to a support material, b) generating hereroduplex structures between a plurality of different messenger RNAs derived from the second sample, wherein the composition or sequence of the RNAs is at least partially unknown, and a plurality of different cDNAs derived from the first sample, wherein the composition or sequence of the RNAs is at least partially unknown, on the other hand, the RNAs or cDNAs being fixed to a support material; and c) identifying or cloning at least one unpaired RNA region within heteroduplex structures from steps (a) and (b), said cloned or identified unpaired RNA region corresponding to a nucleic acid distinct of said samples.

12. A method for identifying proteins or protein domains distinct to a pathology, comprising:

a) hybridizing a population of different messenger RNAs of a first, pathological sample, wherein the nucleic acid composition or sequence of said first sample is at least partially unknown, with a population of different cDNAs derived from a second, healthy sample, wherein the nucleic acid composition or sequence of said second sample is at least partially unknown, b) identifying, from the hybrids formed in (a), at least one nucleic acid comprising an unpaired region, said nucleic acid corresponding to a portion of a gene that is differentially spliced between said samples, and c) identifying the protein or protein domain corresponding to said nucleic acid identified in step (b), wherein said protein or protein domain is distinct to said pathology.

13. A method for identifying nucleic acids or nucleic acid domains distinct to a tumor state, comprising;

a) hybridizing a population of different messenger RNAs of a first, tumor sample, wherein the nucleic acid composition or sequence of said first sample is at least partially unknown, with a population of different cDNAs derived from a second, healthy sample, wherein the nucleic acid composition or sequence of said second sample is at least partially unknown, and b) identifying, from the hybrids formed in (a), at least one nucleic acid comprising an unpaired region, said nucleic acid corresponding to a portion of a gene that is differentially spliced between said samples, and said nucleic acid or a domain thereof being distinct to the tumor state.

14. A method for identifying genetic markers resulting from treatment of a biological sample with a test compound, comprising:

a) preparing at least a first nucleic acid library by hybridizing (I) a plurality of different RNA molecules derived from said biological sample treated with said test compound, wherein the composition or sequence of said different RNA molecules is at least partially unknown, with (ii) a plurality of different cDNA molecules derived from said biological sample untreated with said test compound, wherein the composition or sequence of said different cDNAs is at least partially unknown, wherein said first library comprises nucleic acid molecules comprising sequences corresponding to portions of genes which are differentially spliced in the treated sample as compared to the untreated sample, and cloning, from the hybrids formed, nucleic acids comprising an unpaired region, b) preparing at least a second nucleic acid library by hybridizing (I) a plurality of different cDNA molecules derived from said biological sample treated with said test compound, wherein the composition or sequence of said different cDNA molecules is at least partially unknown, with (ii) a plurality of different RNA molecules derived from said biological sample untreated with said test compound, wherein the composition or sequence of said different RNA molecules is at least partially unknown, wherein said second library comprises nucleic acid molecules cormprising sequences corresponding to portions of genes which are differentially spliced in the treated sample as compared to the untreated sample, and cloning, frorn the hybrids formed, nucleic acids comprising an unpaired region, and c) screening for genetic markers within the first or second library.

15. A method of determining or assessing the toxicity of a test compound to a biological sample, comprising:

a) hybridizing a nucleic acid preparation of the biological sample treated by said test compound, with at least a first and second nucleic acid library, wherein said first library comprises nucleic acid molecules obtained by the method of claim 1 comprising sequences corresponding to portions of genes which are differentially spliced in the un-treated biological sample as compared to the biological sample treated with a standard toxic compound, and said second library comprises nucleic acid molecules obtainable by the method of claim 1 comprising sequences corresponding to portions of genes which are differentially spliced in the biological sample treated with a standard toxic compound as compared to the untreated sample, and b) assessing the toxicity of said test compound by examining the extent of hybridization of said nucleic acid preparation with said different libraries.

16. A method according to claim 15, wherein said biological sample is a hepatocyte culture, either treated or not treated with a test compound, wherein said test compound is a toxic agent.

17. A method according to claim 15, wherein the biological sample is a skin culture either treated or not treated with a test compound, wherein said test compound is a toxic agent or irritant.

18. A method of determining or assessing the therapeutic potential of a test compound with respect to a biological sample, comprising:

a) hybridizing a nucleic acid preparation of the biological sample treated by said test compound, with at least a first and second nucleic acid library, wherein said first library comprises nucleic acid molecules obtained by the method of claim 1 comprising sequences corresponding to portions of genes which are differentially spliced in the un-treated biological sample as compared to the biological sample treated with a standard therapeutic compound, and said second library comprises nucleic acid molecules obtainable by the method of claim 1 comprising sequences corresponding to portions of genes which are differentially spliced in the biological sample treated with a standard therapeutic compound as compared to the un-treated sample, and b) assessing the therapeutic potential of said test compound by examining the extent of hybridization of said nucleic acid preparation with said different libraries.

19. A method of determining or assessing the responsiveness of a patient to a test or treatment, comprising:

a) hybridizing a nucleic acid preparation of the biological sample of the patient, with at least a first and second nucleic acid library, wherein said first library comprises nucleic acid molecules obtained by the method of claim 1 comprising sequences corresponding to portions of genes which are differentially spliced in a responsive biological sample as compared to a non-responsive or poorly responsive biological sample, and said second library comprises nucleic acid molecules obtainable by the method of claim 1 comprising sequences corresponding to portions of genes which are differentially spliced in the non-responsive or poorly responsive biological sample as compared to the responsive biological sample, and b) assessing the responsiveness of the patient by examining the extent of hybridization of said nucleic acid preparation with said different libraries.

20. A method according to claim 19, wherein said test compound is an anti-cancer compound or treatment.

21. A method according to claim 20, wherein said anti-cancer treatment is wild-type p53 gene transfer.

22. The method of claim 1 or 2, wherein said identifying or cloning in step (b) of claim 1 or step (c) of claim 2 further comprises contacting said hybrids with RNAse H.

23. The method of claim 1 or 2, wherein said first and second samples are from cell types in different physiological conditions.

24. The method of claim 14, wherein said markers are associated with the toxicity of said compound.

25. The method of claim 24, wherein said toxic agent is ethanol.

* * * * *